(12) United States Patent
Weinberger et al.

(10) Patent No.: US 7,046,357 B2
(45) Date of Patent: May 16, 2006

(54) APPARATUS FOR MICROFLUIDIC PROCESSING AND READING OF BIOCHIP ARRAYS

(75) Inventors: Scot R. Weinberger, Montara, CA (US); Louis Hlousek, Reno, NV (US)

(73) Assignee: Ciphergen Biosystems, Inc., Fremont, CA (US)

( * ) Notice: Subject to any disclaimer, the term of this patent is extended or adjusted under 35 U.S.C. 154(b) by 191 days.

(21) Appl. No.: 10/769,293

(22) Filed: Jan. 29, 2004

(65) Prior Publication Data

US 2004/0248318 A1    Dec. 9, 2004

Related U.S. Application Data

(60) Provisional application No. 60/444,356, filed on Jan. 30, 2003.

(51) Int. Cl.
*G01N 21/00* (2006.01)
*G01N 33/00* (2006.01)

(52) U.S. Cl. ............... 356/246; 250/287; 250/573; 250/216; 422/68.1; 422/63; 422/66; 422/102; 436/173

(58) Field of Classification Search ............... 356/246, 356/244; 250/282, 287, 573, 216; 436/173; 422/86.1, 63, 65–66, 99, 102, 104
See application file for complete search history.

(56) References Cited

U.S. PATENT DOCUMENTS

| 5,314,825 A | * | 5/1994 | Weyrauch et al. ............ 436/43 |
| 5,739,902 A | * | 4/1998 | Gjelsnes et al. ............. 356/73 |
| 5,777,325 A | * | 7/1998 | Weinberger et al. ........ 250/287 |

(Continued)

FOREIGN PATENT DOCUMENTS

| WO | WO 93/01487 | 1/1993 |
| WO | WO 02/12865 | 2/2002 |

OTHER PUBLICATIONS

Benesch et al., "The determination of thickness and surface mass density of mesothick immunoprecipitate layers by null ellipsometry and Protein $^{125}$ iodine labeling," *Journal of Colloid and Interface Science*, 249:84-90 (2002).

(Continued)

*Primary Examiner*—Gregory J. Toatley, Jr.
*Assistant Examiner*—Sang H. Nguyen
(74) *Attorney, Agent, or Firm*—Townsend and Townsend and Crew LLP

(57) ABSTRACT

A method and a device for detecting an analyte, including a substrate having a chemically selective surface; and a fluidic system disposed on the substrate, the manifold having at least one fluid path in communication with at least a discrete region of the surface, wherein the one fluid path and the discrete region together define a contained sample region on the surface. The fluidic system has a removable portion, wherein the removal of the removable portion of the fluidic system renders the discrete region directly interrogatable by a surface-based analytical tool.

72 Claims, 16 Drawing Sheets

U.S. PATENT DOCUMENTS

| | | | |
|---|---|---|---|
| 6,225,047 B1 | 5/2001 | Hutchens et al. | |
| 6,294,790 B1 * | 9/2001 | Weinberger | 250/397 |
| 6,498,353 B1 * | 12/2002 | Nagle et al. | 250/573 |
| 6,517,783 B1 * | 2/2003 | Horner et al. | 422/102 |
| 6,580,071 B1 * | 6/2003 | Weinberger et al. | 250/287 |
| 6,838,051 B1 * | 1/2005 | Marquiss et al. | 422/63 |
| 2003/0007896 A1 | 1/2003 | Tiefenthaler | |

OTHER PUBLICATIONS

Brandenburg et al., "Grating couplers as chemical sensors: a new optical configuration," *Sensors and Actuators B*, 17:35-40 (1993).

Fattinger, "The bidiffractive grating coupler," *Appl. Phys. Lett.*, 62(13):1460-1462 (1993).

Kunz et al., "Finite grating depth effects for integrated optical sensors with high sensitivity," *Biosensors & Bioelectronics*, 11(6/7):653-667 (1996).

Kunz et al., "Grating couplers in tapered waveguides for integrated optical sensing," SPIE, 2068:313-325 (1993).

Lukosz, "Integrated-optical biochemical sensors and direct immunoassays," *J. Anal. Chem.*, 337:24-25 (1990).

Seifert et al., An integrated optical biosensor (IOBS), *Analytical Letters*, 19(1&2):205-216 (1986).

* cited by examiner

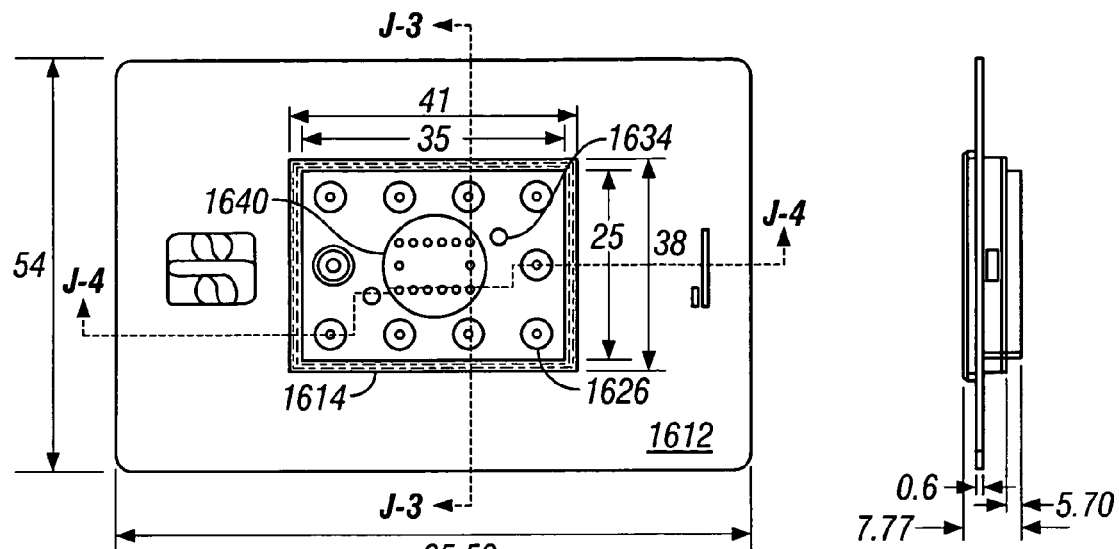
FIG. 6J-1
FIG. 6J-2
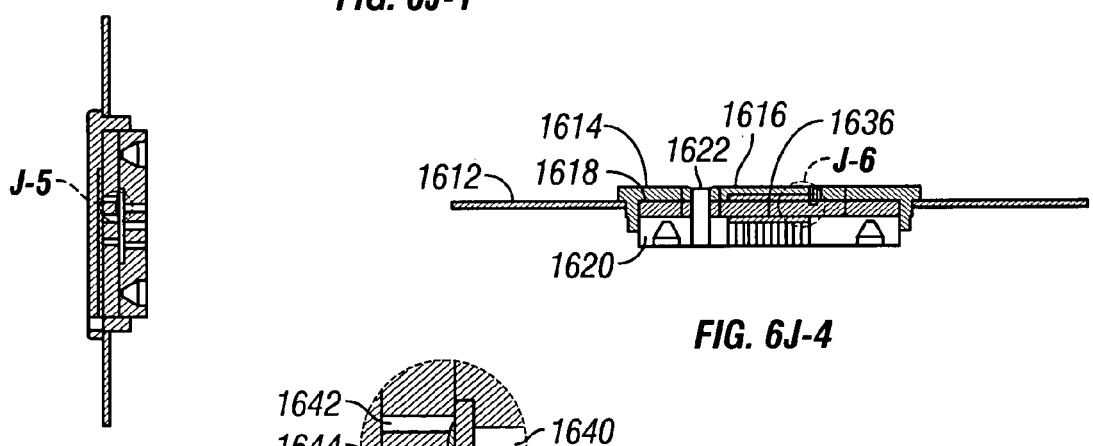
FIG. 6J-4
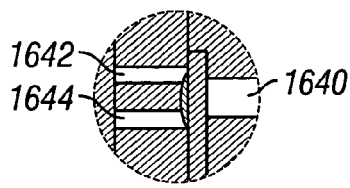
FIG. 6J-5
FIG. 6J-3
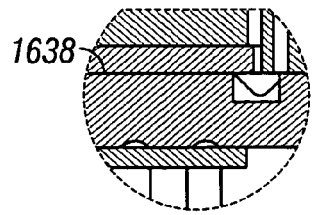
FIG. 6J-6
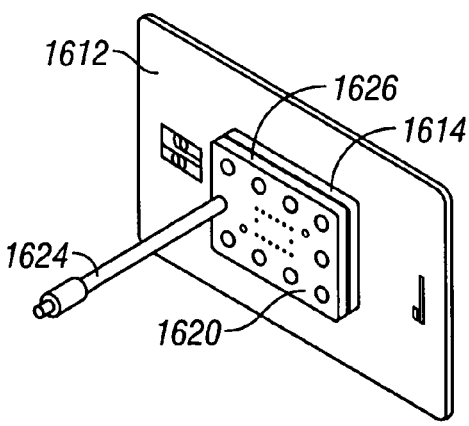
FIG. 6J-7

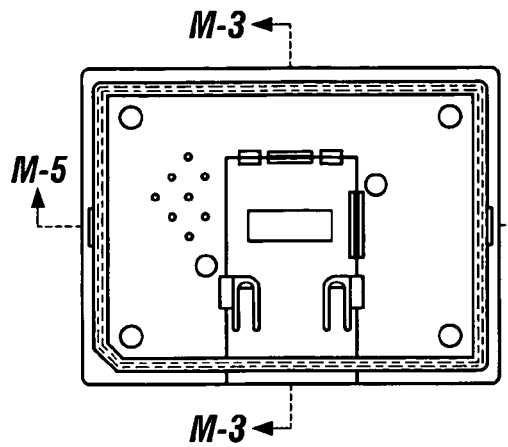
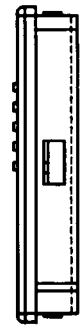
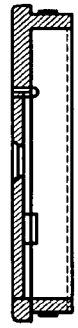
FIG. 6M-1    FIG. 6M-2    FIG. 6M-3
FIG. 6M-4
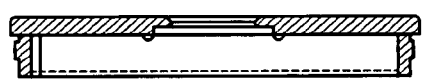
FIG. 6M-5
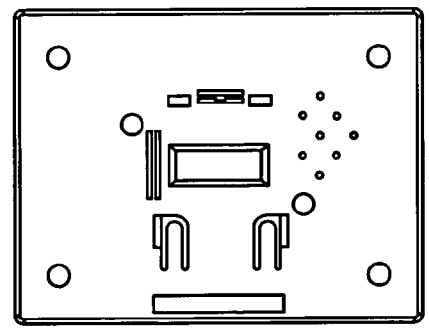
FIG. 6M-6
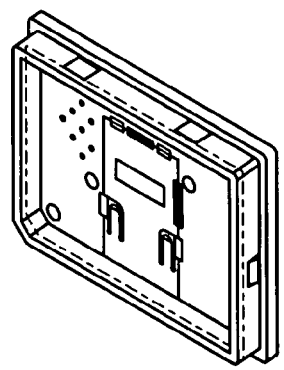
FIG. 6M-7

APPARATUS FOR MICROFLUIDIC PROCESSING AND READING OF BIOCHIP ARRAYS

CROSS-REFERENCES TO RELATED APPLICATIONS

This application claims the benefit of U.S. Provisional Patent Application No. 60/444,356, filed Jan. 30, 2003, which application is incorporated herein by reference in its entirety for all purposes.

BACKGROUND OF THE INVENTION

This invention relates to the field of separation science, analytical biochemistry, mass spectrometry, and biosensors.

The embodiments of this invention have applications in biology and medicine, including analysis of gene functions, differential gene expression, protein discovery, cellular and clinical diagnostics, food product research and quality assurance, pathogen analysis, environmental analysis, drug discovery, toxicology and drug screening.

In the filed of analytical chemistry, a technique that has demonstrated impressive development and popularity during the past decades involves the use of Time-of-Flight Mass Spectroscopy ("TOFMS"). As is the case with most mass spectrometers, a TOFMS system consists of two major components: an ionization source, which corresponds with the sample introduction means; also known as the interface or inlet system and the mass analyzer, which corresponds with the mass measurement and the ion detection portion. The sample introduction system in a laser desorption/ionization TOFMS is configured to receive a sample probe, which introduces the sample into the mass spectrometer. Biochips, protein biochips or ProteinChip® arrays are all examples of different types of sample probes.

While mass spectroscopy has gained popularity in the analytical biochemistry arena, most analysts have focused their skills towards adapting their sample introduction systems and sample probes to fit a particular mass spectrometer's requirements. This approach tends to constraint the analysts to do what is doable, as opposed to allowing the analyst to do what can be done using a mass spectrometer. In a sense, current mass spectroscopy based analytical techniques start from the mass analyzer, and thus impose their constraints on the sample introduction system and the sample probe. So, while many advances have been made in other analytical areas, such as microfluidic-enabled devices, surface scanners and chromatography, these advances have not found their way into the current generation of sample probes and mass spectroscopy systems.

In addition to these problems, the currently available biochip technologies suffer from various limitations, including: the problems associated with the open loop preparation of samples such as slow methods development and poor assay reliability; excessive sample loss due to the loss of analyte to wetted surfaces encountered during sample preparation; and requiring relatively large amounts of precious analytes. In addition to these, other problems of existing analytical techniques include, low resolution, chromatographic separation primarily based upon solid phase extraction, which characteristically has only a single plate of chromatographic resolution, as well as their limited applicability to biomolecular studies, limited throughput, and their not being directly amenable to automation, since most of the preparation and processing is carried out in an open loop manner.

Embodiments of the current invention address these and other problems.

BRIEF SUMMARY OF THE INVENTION

This invention is directed towards a device comprising a biochip with removable microfluidic elements. The microfluidic elements are designed to deliver fluid that can include an analyte to a specific location on the biochip, where the analyte is available to interact with a binding element attached to the biochip surface. The removability of the microfluidic elements makes it possible to interrogate the surface of the biochip, and therefore, any interaction between the analyte and the binding element, by two kinds of detection devices. One detection device is a surface scanner that does not require direct physical communication (DPC) with the array surface while the array is being processed. Such a scanner can be used when the microfluidic portion is in place. For example, the first detection device can involve a grating coupled optical sensor, such as WIOS (wavelength interrogated optical system) or a surface plasmon resonance detector (SPR) that detects real-time binding events between the analyte and the capture molecule while fluid is flowing over the location where the capture molecule is attached. The second detection device involves a surface-based analytical tool (SBAT) that requires direct physical communication. Such a device operates when the microfluidics portion is removed. The second device can involve, for example, mass spectrometry, which requires access to the biochip surface that is achieved by removing the microfluidics portion leaving the biochip surface exposed. Consequently, the device of this invention includes means for fastening the microfluidics portion to the biochip, means for engaging the device with a surface scanning device that operates while the microfluidics portion is attached, and means for engaging the biochip with surface-based analytical tool when the microfluidics portion is removed from the device.

In one aspect, the present invention provides a device having a substrate that has a chemically selective surface and a fluidic system located on the substrate. The fluidic system includes at least one fluid path in communication with at least a discrete region of the surface, such that the one fluid path and the discrete region together define a contained sample region on said surface. The device also includes a removable fluidic system portion, as well as structures for fastening the fluidic system to the substrate; and structures for engaging a first detection system, where the device is removably insertable into the detection system. The first detection system includes structures for interrogating the substrate surface when the fluidic system portion is integrated with the device. The device also includes structures for engaging a surface-based analytical tool. The surface-based analytical tool includes structures for interrogating the substrate surface as a result of removal of the fluidic system portion.

In one embodiment, the substrate is adapted for use in a first detection system, where the detection system includes an optical device, an electrochemical device, an atomic force device, a radio frequency device, a piezoelectric vibrating member, a resonant cantilever device, or combinations thereof.

In another embodiment, the substrate is adapted for use in a surface-based analytical tool that is a desorption spectrometer or an atomic force device.

In one aspect, the substrate is made of an optically transparent material. In another aspect, the substrate is made of an optically transparent material and its surface includes a material with a higher refractive index than the substrate. The higher refractive index material may be a metal oxide, such as for example, $Ta_2O_5$, $TiO_2$, $ZrO_2$, $HfO_2$, $SiO_2$, and $Si_3N_4$.

In another aspect, the substrate includes a grating coupler waveguide that couples through the discrete region.

In another aspect, the substrate includes structured electrodes that couple through the discrete region.

In one aspect, the chemically selective surface includes a chromatographic capture reagent.

In another aspect, the chemically selective surface includes a biospecific capture reagent.

In another aspect, the chemically selective surface includes a reactive moiety capable of binding a capture reagent.

In another aspect, the chemically selective surface includes a material that supports desorption and ionization of adsorbed species upon laser irradiation.

In one aspect, the sample region includes a chromatographic stationary phase. The stationary phase is configured to perform thin layer, open tubular, capillary, packed, gel or retentate chromatography.

In one aspect, the stationary phase is the chemically selective surface of the region.

In another aspect, the device includes several stationary phases arranged serially within the device, so as to perform multi-stage chromatography.

In one aspect, the fluid path has an inlet port configured to accept fluid from a fluid delivery system.

In another aspect, the fluidic system has a first solid portion and a gasket, where the gasket is in contact with the substrate.

In another aspect, the at least one fluid path is in communication with several discrete portions of the surface.

In another aspect, the fluid path has at least one diaphragm valve.

In another aspect, the fluidic system has several fluid paths in fluid communication with the same sample region.

In another aspect, the fluidic system has structures for fastening it to the substrate.

In one aspect, the fluidics system includes an electrophoretic separation column.

In one aspect, the entire fluidic system is removable from the device.

In one aspect, the structures for fastening the fluidic system to the substrate include a holder that receives the fluidics system and receives the substrate between the fluidics system and the holder.

In another aspect, the structures for fastening include a holder that receives the fluidics system and receives the substrate between the fluidics system and the holder and further includes a pin that holds the fluidics system to the holder.

In another aspect, the structures for fastening include a first frame that receives the fluidics system and a second frame comprising a surface complementarily shaped with respect to the first frame to securely hold the fluidics system inside the first frame.

In one aspect, the removable fluidics portion is peelably removable from the device.

In another aspect, the removable fluidics portion is removably fastened to the device by mechanical fasteners, adhesives or frangible attachment.

In another embodiment, the present invention provides a process for detecting an analyte. The process includes: providing a substrate having a chemically selective surface, where the substrate is attached with a fluidic system; delivering a sample including an analyte using the fluidic system to at least one sample region on the substrate; monitoring physicochemical changes of the surface in response to the analyte; removing a portion of the fluidic system to render a portion of the surface directly interrogatable by a surface based analytical technique; and detecting physicochemical changes of the surface region. The method may also include interrogating the surface after the removal of a portion s of the fluidic system using LDI-MS.

The substrate with the chemically selective surface can include a chemically selective surface having a reactive moiety and the sample region includes a capture reagent that is bound by the reactive moiety. The capture reagent may be bound by the moiety by physi-sorption. The process may also include delivering a conditioning fluid to the surface after the delivering the sample. The process may also include delivering a reagent to selectively functionalize the surface after delivering the sample. The process may also include delivering the sample to several discrete locations on the surface.

The sample that is delivered can be one of several samples and the sample region can be one of several different sample regions and then the delivering can include delivering each of the several samples to the different sample regions. When the setup is used for LDI-MS the fluidic system may be used to deliver a matrix solution to the sample region before directing energy at the sample region.

The monitoring of the physicochemical changes of the surface includes optical monitoring, electrochemical monitoring, atomic force monitoring, a radio frequency monitoring, a piezoelectric vibrating member monitoring, a resonate cantilever device monitoring, and combinations of these. The optical-based monitoring is configured to monitor changes in properties of polarization of light caused by interaction of light with the surface. The properties that are monitored include fluorescence, luminescence, chemiluminescence, absorbance, reflectance, transmittance, birefringence, refractive index and combinations thereof.

The optical monitoring may include using an optical-based device that is configured to detect changes in the refractive index at the surface, such as for example, a grating coupler waveguide device. The grating coupler waveguide device is interrogated by varying the wavelength of incident radiation at a fixed angle and determining the wavelength of maximum coupling. Alternately, the grating coupler waveguide device is interrogated by varying the angle of the incident light of a fixed wavelength and determining the angle of maximum coupling. Yet alternately, the grating coupler waveguide device is interrogated by illuminating the grating coupler device with light having a range of wavelengths and determining the wavelength of maximum coupling by measuring the wavelength of the coupled light. Or, the grating coupler waveguide device is interrogated by illuminating the grating coupler device with light of a fixed wavelength over a range of angles and determining the angle of the coupled light. Or, the grating coupler waveguide device is interrogated by a combination of: varying the wavelength of incident radiation at a fixed angle and determining the wavelength of maximum coupling, varying the angle of the incident light of a fixed wavelength and determining the angle of maximum coupling, illuminating the grating coupler device with light having a range of wavelengths and determining the wavelength of maximum coupling by measuring the wavelength of the coupled light, and illuminating the grating coupler device with light of a fixed wavelength over a range of angles and determining the angle of the coupled light.

The process for detecting an analyte can also include providing a substrate that includes structures for rendering the substrate compatible with a device for monitoring physicochemical changes of the surface. The monitoring includes an optical monitoring and the structures include an optically transmissive path communicating with the surface. The path can be a window, a lens, a prism, a surface planar waveguide or an optical fiber. Alternately, the monitoring includes an optical monitoring and the structures can include a polarizer, a lens, a mirror, a diffraction grating, a wave plate, an attenuator, an interferometer and combinations thereof.

Alternately, the monitoring is an electrochemical monitoring and the structures include electrodes in electrical communication with said surface. Yet alternately, the monitoring is performed using an atomic force microscope (AFM) and the structures include AFM probe or port for accepting an AFM probe in physical communication with the surface.

Alternately, the monitoring includes using a radio frequency device and the structures include a radiofrequency waveguide in radio frequency communication with the surface.

Furthermore, the process for detecting an analyte may also include the prior electrophoresis of the sample, the electrophoresis including capillary denaturing, nascent, free zone, isoelectric focusing, isotachophoresis, gel electrophoresis, or combinations thereof. In addition, the process for detecting an analyte includes: providing a device having a substrate and a fluidic system disposed on the substrate, where the device includes an electrophoresis medium on the substrate surface; electrophoresing a sample including analytes through the medium, such that the analytes are electrophoretically separated through the medium; detecting in real-time the electroporesis of the sample by a surface scanner; and; further detecting the separated analytes by laser desorption/ionization mass spectrometry.

The processes described above can be carried out in system as described below. Such a system includes a device having a substrate with a fluidic system; and devices for interrogating the substrate surface when the fluidic system portion is coupled with the device. In connection with the device, the substrate has a chemically selective surface and the fluidic system is disposed on the substrate. The fluidic system includes: at least one fluid path in communication with at least a discrete region of the surface, such that wherein the one fluid path and the discrete region together define a contained sample region on the surface. The fluidic system includes a removable fluidic system portion. As described above, The device also includes structures for fastening the fluidic system to the substrate; structures for engaging a first detection system, such that the device is removably insertable into the detection system; and where the first detection system includes structures for interrogating the substrate surface when the fluidic system portion is integrated with the device. The device also includes structures for engaging a surface-based analytical tool, where the surface-based analytical tool includes structures for interrogating the substrate surface as a result of removal of the fluidic system portion.

In one embodiment, the structures for interrogating include an optical device and the structures for engaging include an optically transmissive path communicating with the surface, where the path may be a window, a lens, a prism, a surface planar waveguide or a fiber optic.

The optical device is configured to monitor changes in properties of the polarization of light caused by interaction of light with the surface. Alternately, the optical device is configured to monitor properties of the surface selected, which can include the properties related to fluorescence, luminescence, chemiluminescence, absorbance, reflectance, transmittance, birefringence, refractive index and combinations thereof.

Alternately, the optical device is configured to detect changes in the refractive index at the surface.

In one embodiment, the substrate has a grating coupler waveguide. In one aspect, the waveguide is interrogated by varying the wavelength of incident radiation at a fixed angle and determining the wavelength of maximum coupling. Or, the waveguide is interrogated by varying the angle of the incident light of a fixed wavelength and determining the angle of maximum coupling. Or, the waveguide is interrogated by illuminating the grating coupler device with light having a range of wavelengths and determining the wavelength of maximum coupling by measuring the wavelength of the coupled light. Or, the waveguide is interrogated by illuminating the grating coupler device with light of a fixed wavelength over a range of angles and determining the angle of the coupled light. Or, the waveguide is interrogated by a combination of these interrogation techniques.

In one embodiment of the system described above, the device for interrogating includes an optical device and the means for engaging the device can include a polarizer, a lens, a mirror, a diffraction grating, a diffractive element, a wave plate, an attenuator, an interferometer and combinations thereof.

Alternately, the device for interrogating includes an electrochemical device and the means for engaging the device includes electrodes in electrical communication with the surface. Yet alternately, the device for interrogating includes a radio frequency device and the means for engaging the device include a radiofrequency waveguide in radio frequency communication with the surface.

In another embodiment, the method includes providing a substrate having a chromatographic stationary phase in the sample region, flowing the sample across the chromatographic surface, and chromatographically separating the analyte in the sample region. The stationary phase is configured to perform thin layer, open tubular, capillary, packed, gel or retentate chromatography. In one embodiment, the stationary phase is contained in a channel in the fluidic manifold as a material that is filling the channel or coating the channel. In another embodiment, the chemically selective surface of the region includes the stationary phase. In yet another embodiment, the stationary phase is one a plurality of stationary phases to enable the performance of multi stage chromatography.

In one embodiment, the chromatographic separation includes a Reverse Phase, ion exchange, mixed mode, normal phase, immobilized metal affinity capture, affinity capture, or combinations thereof.

In another embodiment, the chromatographic separation includes monitoring the chromatographic surface at a plurality of locations; and detecting analytes bound to the surface at the plurality of locations.

In another embodiment, the method includes the prior electrophoresis of the sample, the electrophoresis including capillary denaturing, nascent, free zone, isoelectric focusing, isotachophoresis, gel electrophoresis, or combinations thereof.

In another aspect, the present invention provides a method of detecting an analyte, including providing a device having a substrate that has a chromatographic surface; flowing a sample of analytes across the surface, whereby analytes are chromatographically separated across, and bound to, the surface; and detecting the analytes bound to the surface by laser desorption/ionization mass spectrometry.

In another aspect, the present invention provides a device for detecting an analyte, including a substrate having a chromatographic surface; means for flowing a sample comprising analytes across the surface; means for chromatographically separating the analytes across the surface, to form analytes that are chromatographically separated across, and bound to, the surface; and means for detecting the analytes bound to the surface by laser desorption/ionization mass spectrometry.

In another aspect, the present invention provides a method of detecting an analyte, including: providing a device comprising a substrate and a fluidic manifold disposed on the substrate, the device having an electrophoresis medium on the substrate surface; electrophoresing a sample comprising analytes through the medium, whereby analytes are electrophoretically separated through the medium; detecting in real-time the electroporesis of the sample by a surface scanner; and further detecting the separated analytes by a secondary SBAT.

In another aspect, the present invention provides a device, including a substrate and a fluidic system disposed on the substrate. The fluidic system has at least one fluid path in communication with at least a discrete region of the surface of the substrate, wherein the one fluid path and the discrete region together define a contained sample region on the surface. The fluidic system has a removable portion and a remaining portion of the fluidic system that remains after removal of the removable portion. The remaining portion has at least one electrostatic and/or pneumatic element. The device includes structures for engaging a surface based analytical tool (e.g., a laser desorption/ionization probe) interface. The surface-based analytical tool has means for interrogating the substrate surface as a result of removal of the fluidic system portion.

For a further understanding of the nature and advantages of the invention, reference should be made to the following description taken in conjunction with the accompanying drawings.

BRIEF DESCRIPTION OF THE DRAWINGS

FIG. 6J is a drawing of various details of FIG. 6H.

FIG. 6M is a detailed drawing of the frame of FIG. 6J.

DETAILED DESCRIPTION OF THE INVENTION

Figure 1:
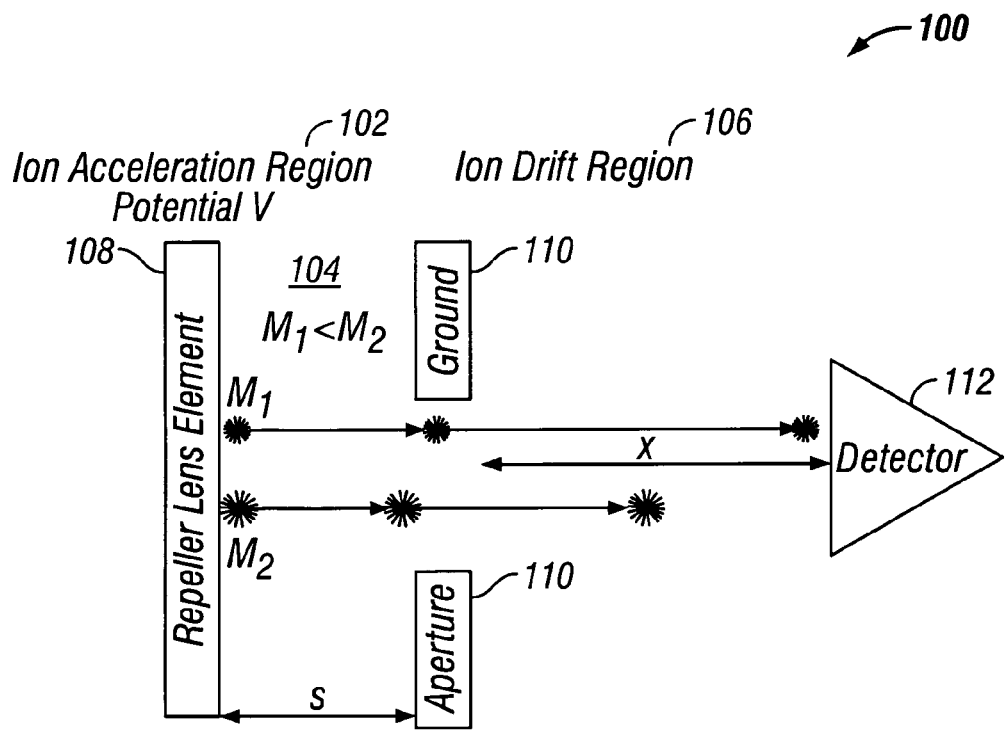
FIG. 1 is a diagram of a single-stage ion optic, linear, constant-energy mass spectrometer.

I. Apparatus for Microfluidic Processing of Biochip Arrays
    A. Biochip Technology Biochips include a surface which has capture molecules attached, and may include arrays having specific molecules at identifiable locations. The surface and/or array locations are interrogated for the presence or interactions of analyte molecules with the capture molecules. The interrogation includes surface scanning involving various techniques. One technique involves the interrogation techniques without physically communicating or touching the chip surface. Other techniques perform the surface interrogation by using a surface-based analytical tool, where the interrogation involves physically contacting the surface of the chip where the analyte molecules are attached.

Techniques without physically communicating or touching the chip surface include optical methods, electrochemical methods, radio frequency methods, methods involving a piezoelectric vibrating member, resonant cantilever methods and combinations thereof. Optical methods include, for example, detection of fluorescence, luminescence, chemiluminescence, absorbance, reflectance, transmittance, birefringence or refractive index (e.g., surface plasmon resonance, ellipsometry, a resonant mirror method, a diffraction grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Techniques that require physical access to the chip surface include gas phase ion spectrometry methods and atomic force microscopy. Of particular interest is the use of mass spectrometry and, in particular, SELDI.

Described below are bio chip substrates and devices that are adapted for interrogation by both of these techniques, namely surface-based and non-physically communicating techniques. The adaptations include appropriate structures for engaging the particular interrogating device, and are described below.

Biochips, in general, comprise a substrate to which array of capture molecules has been attached, each at a discrete and identifiable location on the substrate surface in such a manner as to be addressable by a detection method of choice. The capture molecules typically are biomolecules, such as nucleic acids, proteins, carbohydrates or lipids. They also can be small organic molecules. When exposed to an analytic sample, analytes in the sample can bind to a capture molecule on the surface for which it has affinity. The capture or interaction between an analyte molecule and a capture molecule is detected or characterized by any of a variety of means, as will be described herein. One embodiment of the present invention is directed towards a novel combination of a microfluidic system and a biochip array, such as for example, a SELDI ProteinChip® Array, that functions to deliver a fluid sample to defined locations on the array surface.

1. Chips Adapted for Sensing without Physical Communication

As set forth above, preferred chips adapted for interrogation without physical communication include SPR and diffraction grating coupled waveguide chips. Biochips for SPR have three layers: A transparent substrate, a very thin coating of rare earth metal, such as gold, attached to the substrate surface and an affinity layer is applied to the gold coating. SPR-based detection involves directing light through the transparent substrate to the underside of the rare earth metal layer. Interaction of analytes with the affinity layer, such as binding or release of the analyte from an affinity molecule, change the refractive index of the affinity layer. Using SPR, the determination involves determining the variation in wavelength of absorbance for a given angle of incidence of light incident the gold layer, or determining the variation in the angle of maximum absorbance for a given wavelength of light incident on the gold layer. This variation is representative of the amount of analyte. Another variation is grating coupled SPR. In this case the substrate comprises a diffraction grating on which the sample is placed. Light is directed from the top to the surface of the chip, where the analyte is bound, and the light is reflected off the diffraction grating and detected SPR-based biosensors monitor interactions by measuring the mass concentration of biomolecules close to a surface. The surface is made specific by attaching one of the interacting partners. Sample containing the other partner(s) flows over the surface, and when molecules from the sample bind to the surface, the local concentration changes and an SPR response is measured. The response is directly proportional to the mass of molecules that bind to the surface. The sensor chip, in general, is a glass substrate covered with a layer of gold. On some chips, the gold is covered with a layer of a material (e.g., carboxymethylated dextran) which provides a matrix for covalent attachment of proteins and other molecules as well as forming a hydrophilic environment where the interaction will take place. Other sensor chips include specialized surfaces designed to optimize the environment for specific interaction studies.

Biochips having diffraction grating coupled waveguides are adapted for WIOS. As is described below, the detection principle of the WIOS chips is the grating-coupler sensor. The feature area on a substrate is grooved to form the grating and a thin (~200 nm) high index layer (planar waveguide) is deposited on the substrate. The affinity layer is deposited on top of the waveguide layer. A light beam of a given wavelength travels though the substrate and impinges on the planar waveguide at such an angle that it is diffracted along, and thereby coupled into, the waveguide. Light from the beam can out-couple either through the same grating or a second grating. The second grating may have a different period or thickness than the first grating. The light diffracted light out of the waveguide is directed onto a photo detector. An evanescent field extends above the diffraction grating and interacts with the affinity layer. Changes in the RI of the affinity layer change the wavelength or angle at which the light is optimally coupled into and/or out of the waveguide. By changing the thickness of the planar waveguide, its refractive index, or introducing a buffer layer of appropriate index and thickness between the waveguide and affinity layer, it is possible to adjust the penetration depth of the evanescent field. This effect might be utilized to tailor response for thick or thin affinity layers. The detector measures the out-coupled light to measure the change in the RI of the layer.

In WIOS, the wavelength of the light provided for in-coupling into the waveguide is periodically varied. The detector detects the intensity of the light that is out-coupled from the waveguide at each wavelength. The detector signal is further processed to determine the wavelength of maximum intensity. Interactions of analytes with the chip surface change the refractive index which, in turn, changes the wavelength of maximum coupling for a given angle of incidence.

In another grating coupler method the wavelength is fixed and the angle of incidence is periodically varied. The detector detects the intensity of the light that is out-coupled from the waveguide at each angle. The detector signal is further processed to determine the angle of maximum intensity. Interactions of analytes with the chip surface change the refractive index which, in turn, changes the angle of maximum coupling for a given wavelength.

2. Chips Adapted for Sensing by Surface-Based Analytical Tool

Desorption spectrometry, e.g., laser desorption/ionization mass spectrometry, and atomic force microscopy are two methods that require direct access to the surface for scanning.

Biochips for mass spectrometry are adapted as probes that engage a probe interface of a mass spectrometer. Probe in the context of desorption spectrometry (e.g., mass spectrometry) refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A probe generally has a solid substrate (either flexible or rigid) comprising a sample presenting surface on which an analyte is presented to the source of ionizing energy.

The invention is particularly applicable to and will be explained by reference to a protein biochip array. However, it should be realized the invention is equally applicable to any generalized biochip array, or arrays used to monitor and detect analytes, and is not to be limited for use only with protein biochip arrays.

Currently available SELDI technology enables selective retention of polypeptides and other molecules on protein biochip array surfaces by means of distinct chromatographic or bioaffinity surfaces. Protein biochip arrays are available with a variety of chromatographic surfaces including Reverse Phase, cationic, anionic, and metal affinity. Bioaffinity surfaces used for antibody-antigen, DNA-protein, receptor-ligand and whole cell capture are also currently available.

Once proteins are bound to the array surface, a set of buffers is used to wash away unbound proteins and other elements of the original sample. A laser desorption/ionization time-of-flight based protein biochip reader, such as for example, those available from the assignee herein, then detect proteins retained on the array surface.

In such a reader, the process begins when a laser desorbs, and ionizes, proteins from the array surface. Once desorbed from the array surface, the ions are accelerated through the flight tube of the protein biochip reader and are detected by a detector. The velocity at which the ions are accelerated through the flight tube to the detector is a function of ion mass-to-charge ratio; smaller ions will reach the detector faster than large ions. The raw data produced by the TOF-MS-based protein biochip reader plots peak intensity against time-of-flight, which can be converted to M/Z or molecular weight.

The protein biochip reader enables researchers to identify and differentiate proteins bound to protein biochip array surfaces according to their respective ion mass to charge ratios. Protein biochip readers allow the researchers to analyze very small amounts of protein from native biological samples, selectively captured on a protein biochip array. Selective protein retention combined with the ability to assess a protein's molecular weight enables the identification of hundreds of unique proteins from a single sample. In addition, chemical and biochemical processing can be included at any step throughout the SELDI process to enhance the knowledge gained form a set of experiments.

Protein biochip readers and systems produce data compatible with all major protein databases. Thus, proteins can be quantified by plotting peak intensity values against peptide or protein standard quantities.

Figure 6:
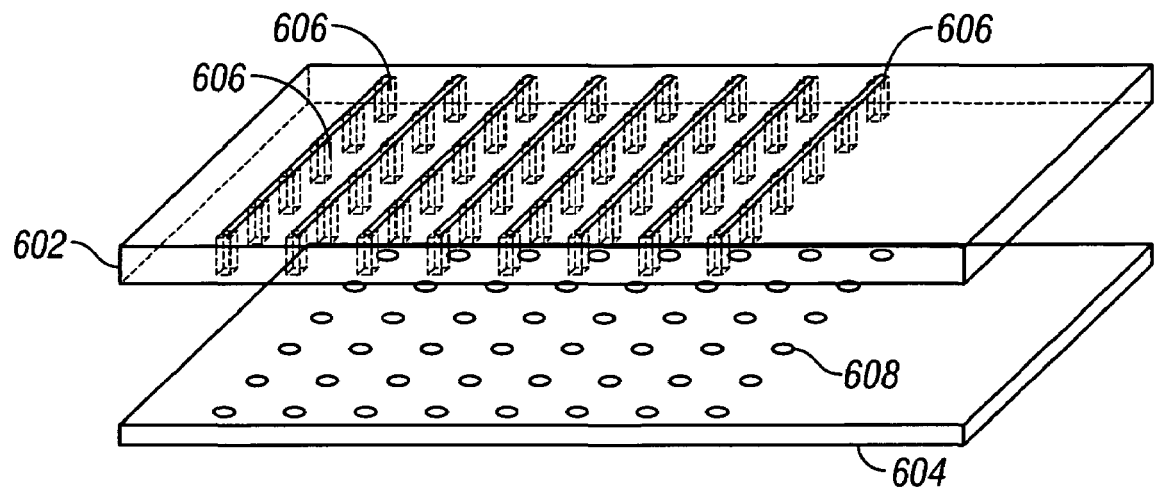
FIG. 6 is a diagram of a fluidic enabled protein biochip array system.
Figure 6A:
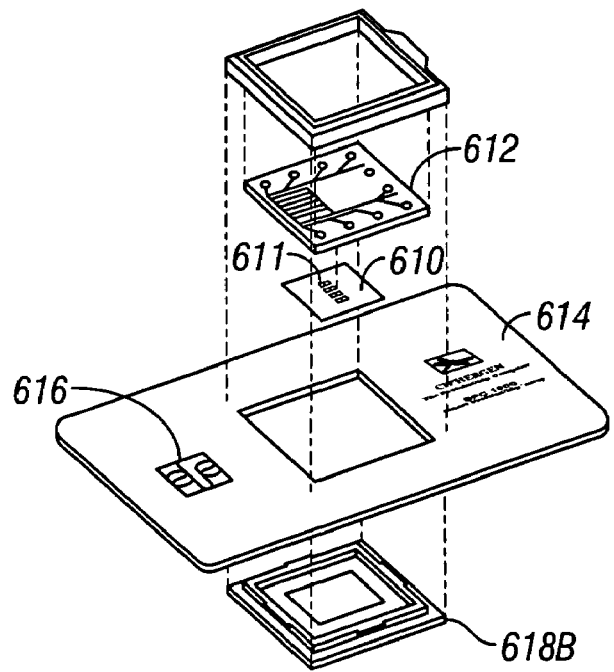
FIG. 6A is an unassembled view of a fluidic enabled protein biochip array system according to an embodiment of the present invention.
Figure 6B:
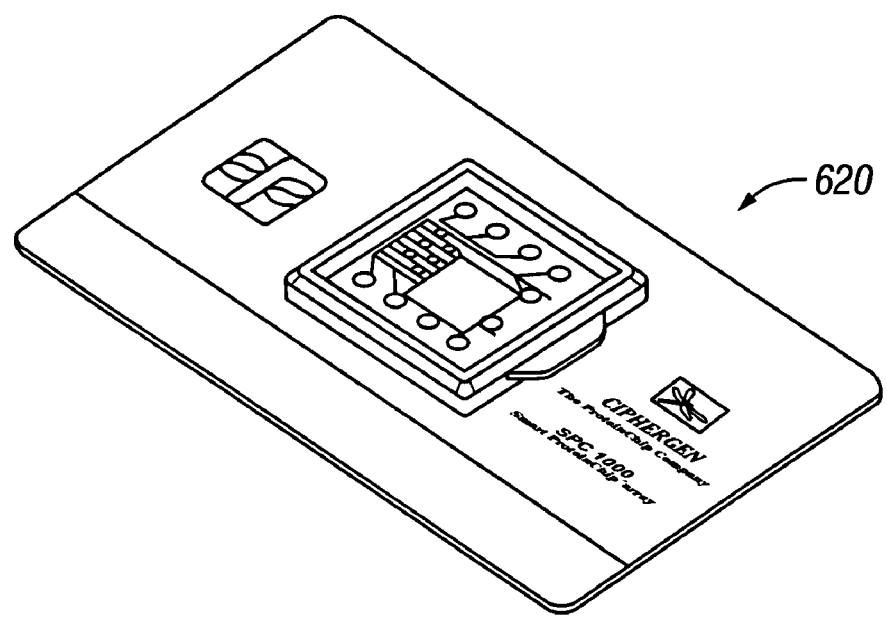
FIG. 6B is a diagram of an assembled view of the chip array system of FIG. 6B.
Figure 6C:
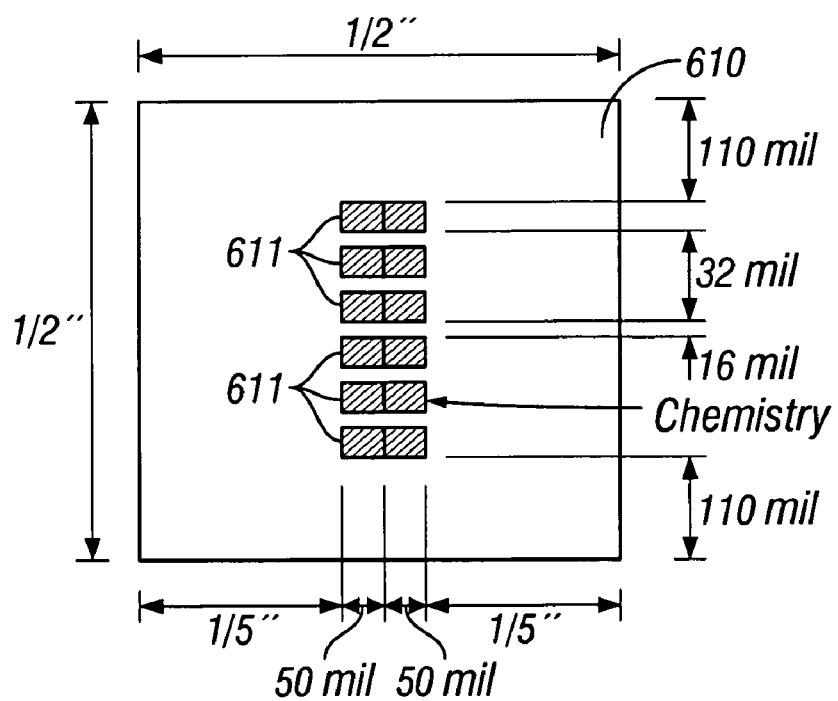
FIG. 6C is a diagram of an embodiment of the substrate of the present invention.
Figure 6D:
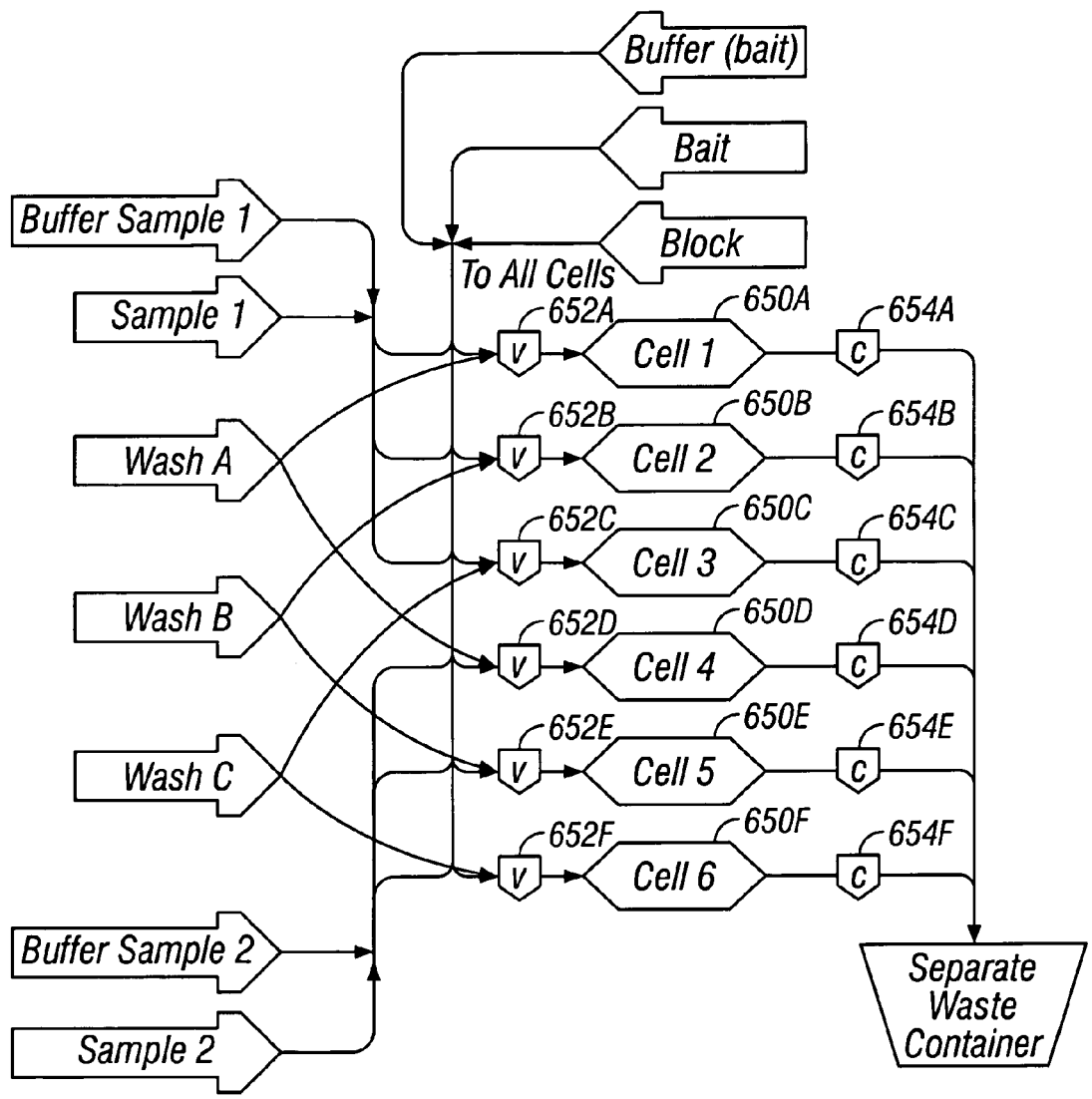
FIG. 6D is a schematic diagram of an embodiment of the fluidic system of the present invention.
Figure 6E:
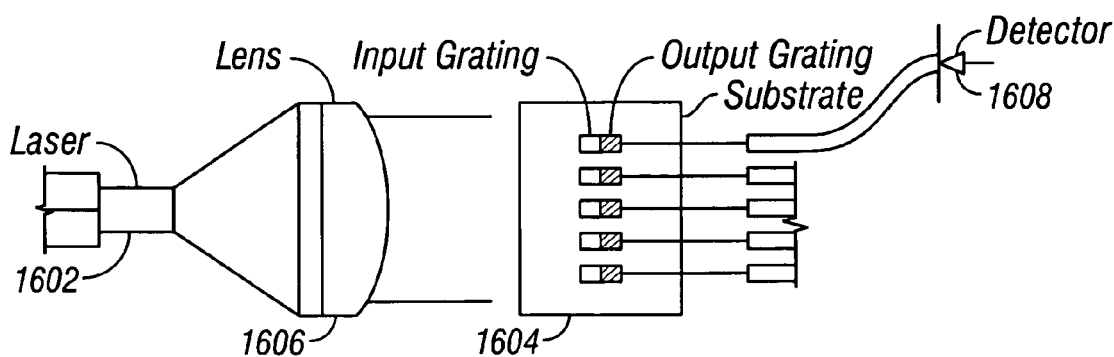
FIG. 6E is an exemplary diagram of an embodiment of a surface scanner system in accordance with the present invention.
Figure 6F:
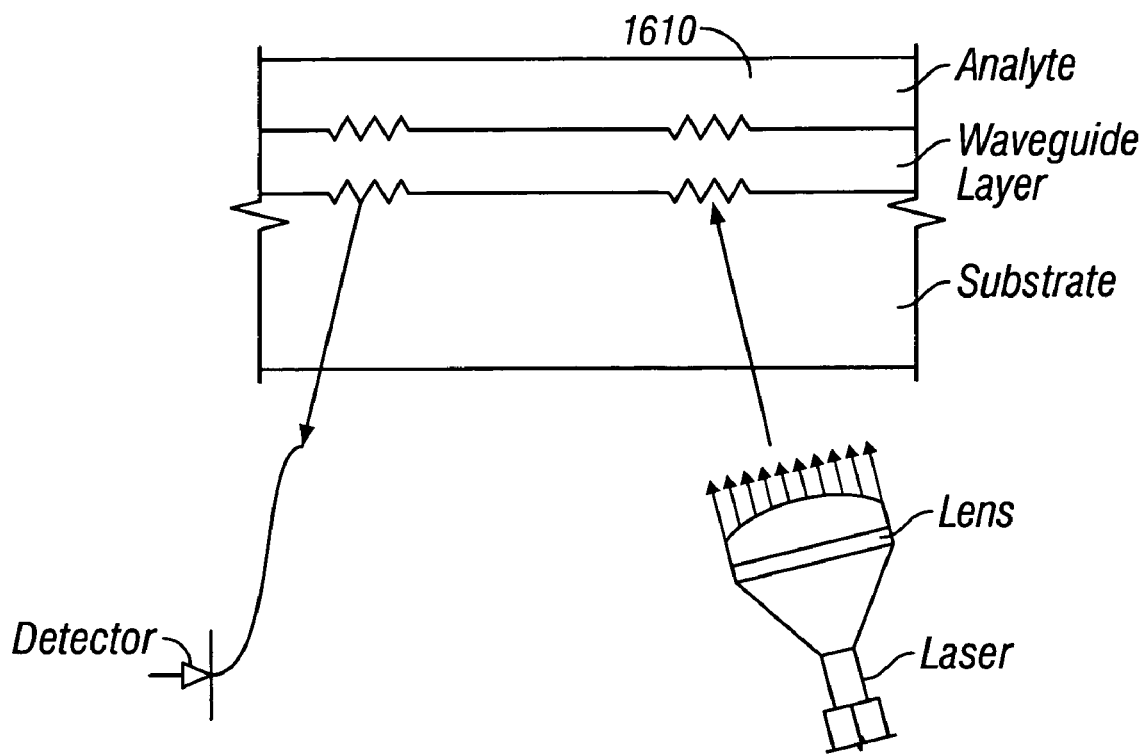
FIG. 6F is an exemplary operational diagram of one of the sensing pads of FIG. 6E.
Figure 6G:
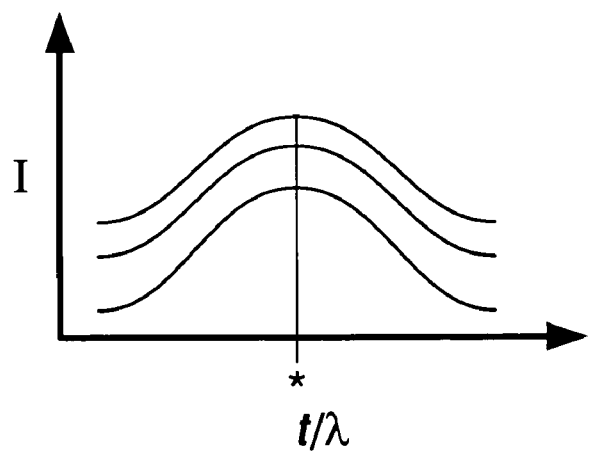
FIG. 6G is a graph of an exemplary detector signal.
Figure 6H:
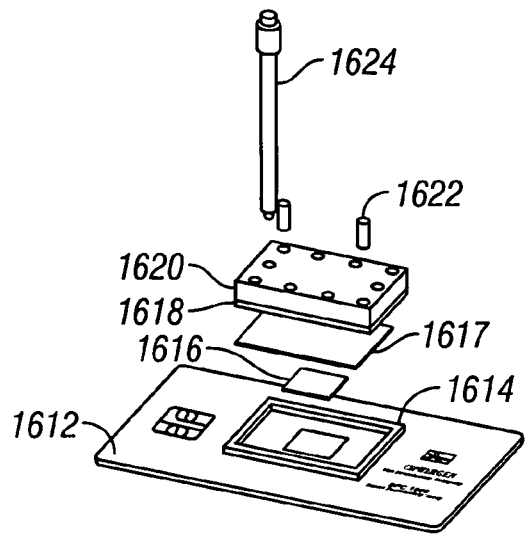
FIG. 6H is an exploded assembly diagram of an alternate fluidic enabled chip array system according to an embodiment of the present invention.
Figure 6I:
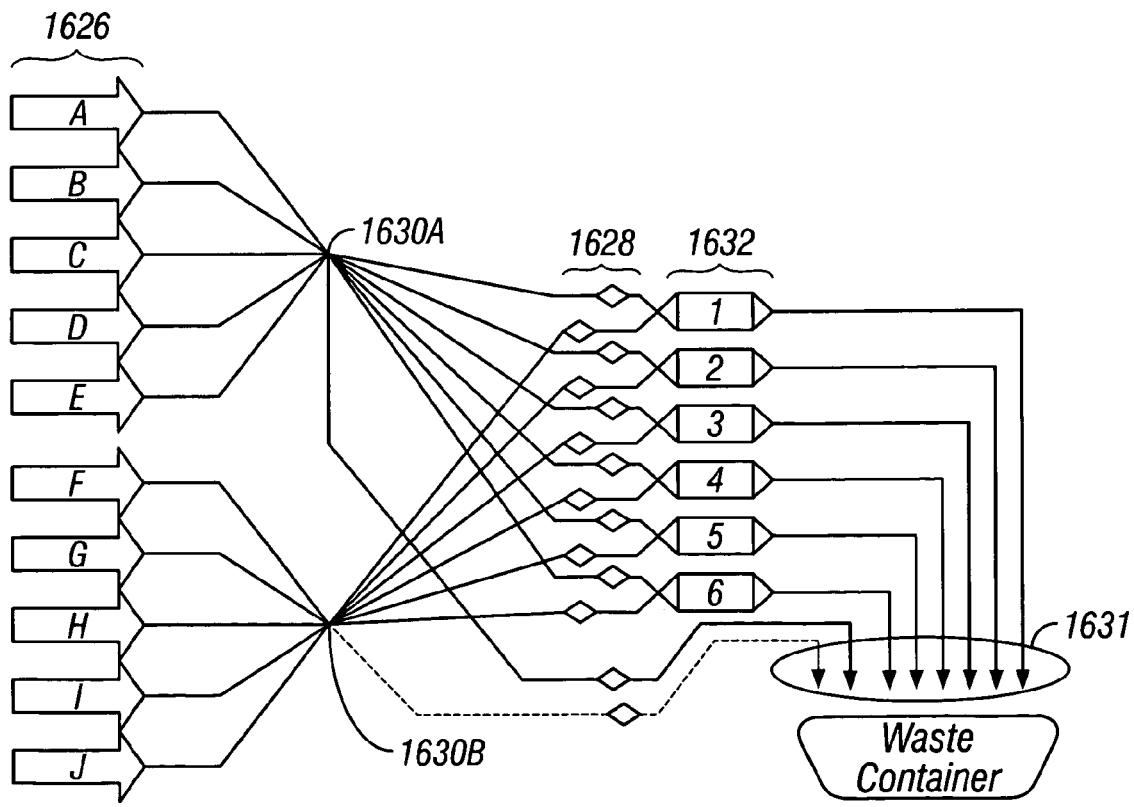
FIG. 6I is an exemplary schematic of the fluidic system layout of FIG. 6H.
Figures 1, 6K:
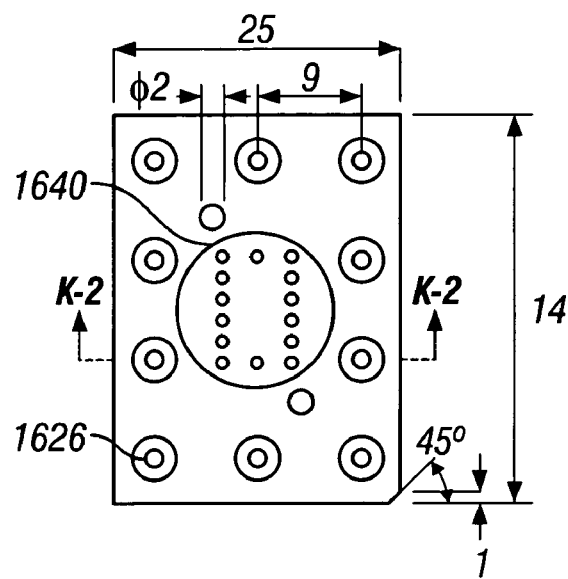
FIG. 6K is a detailed drawing of the first manifold plate of FIG. 6J.
Figures 2, 6K:
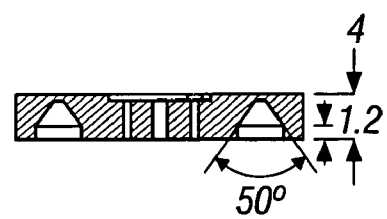
Figures 3, 6K:
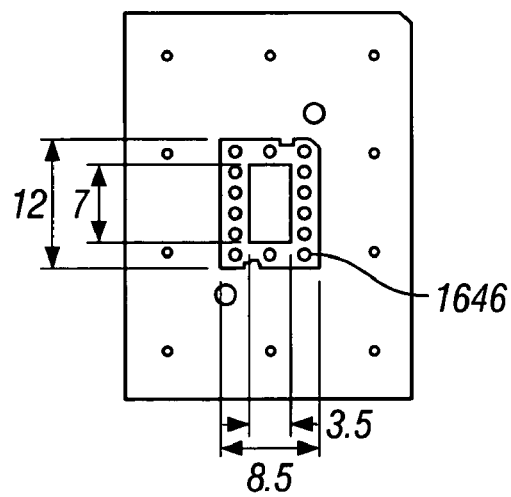
Figures 4, 6K:
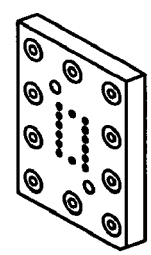
Figures 1, 6L:
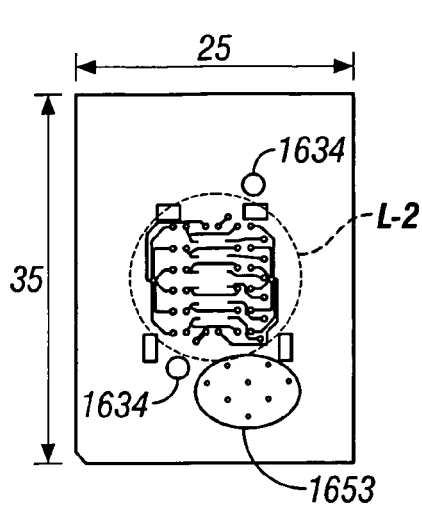
FIG. 6L is a detailed drawing of the second manifold plate of FIG. 6J.
Figures 3, 6L:
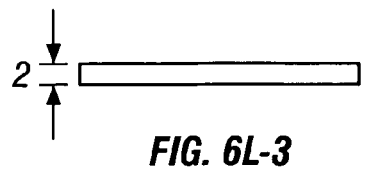
Figures 4, 6L:
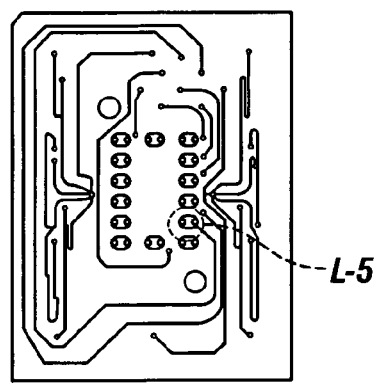
Figures 2, 6L:
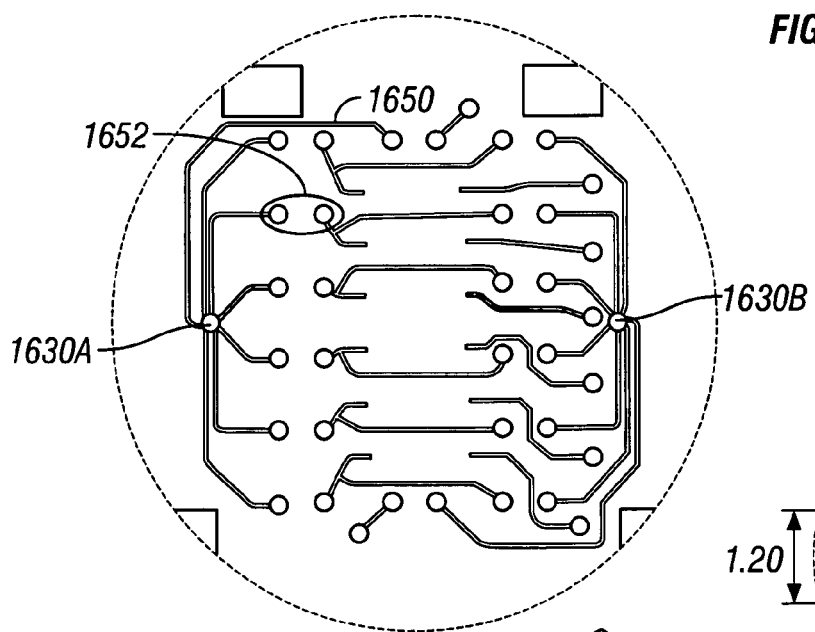
Figures 5, 6L:
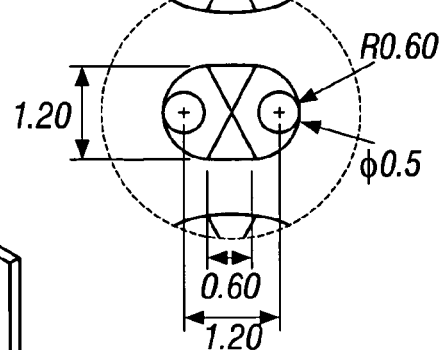
Figures 6, 6L:
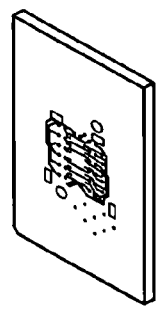

FIG. 5 shows various subsystems involved in the processing of protein biochip arrays. Using currently available systems, the determination of the mass of the protein samples, requires a few steps, including sample crystallization, sample ionization, flight through a vacuum tube, and detection of the ionized proteins. Protein biochip arrays 502 are placed in a carrier 504, and after washing off non-specifically bound proteins and other contaminants from the protein biochip array 502, an energy absorbing molecule (EAM) solution is applied 506 and allowed to dry, during which time minute crystals form on the array. These crystals contain the EAM and the proteins of interest. After inserting the protein biochip Array 502 into the protein biochip reader 508, a laser beam is focused upon the sample, which causes the proteins embedded in the EAM crystals to desorb and ionize. Released ions then experience an accelerating electrical field which causes them to fly through a vacuum tube, towards the ion detector. Finally, ionized proteins are detected and an accurate mass is determined based on the time of flight. Further details of the use and processing of protein biochip arrays are set forth in a co-pending U.S. patent application Ser. No. 09/100,708, entitled: "RETENTATE CHROMATOGRAPHY AND PROTEIN BIOCHIP ARRAYS WITH APPLICATIONS IN BIOLOGY AND MEDICINE," the disclosure of which is herein incorporated by reference in its entirety for all purposes.

B. Microfluidics Elements

Described below is the fluidic system in general and its attachment with the biochip substrate. Also described are the fluidic system's layout, operation and various details of the delivery and control of the fluids from their source onto the substrate surface, including its addressable locations.

As is shown in FIG. 6, a device for identifying an analyte includes a fluidic manifold 602 that is applied to a protein biochip array 604. The manifold 602 includes voids 606 that are in contact with areas 608 on the surface of the biochip 604. The area of contact of the voids defines flow cell volumes and active areas (regions) on the chip's surface. Conduits within the manifold connect to these flow cells permitting various fluids to be brought in contact with and to wash over the regions. Conduits are provided for the exit of fluids that are introduced to the regions.

The manifold 602 may be designed so that some conduits connect to multiple flow cells and others connect only to individual flow cells. Fluids introduced through the conduits that connect multiple flow cells would flow through all the connected flow cells. The interconnection may be in series or in parallel. Fluids introduced to conduits that connect to only one flow cell would flow through only that region.

The manifold 602 may incorporate various fluidic components (e.g., valves, restrictors, heat exchangers, mixers, etc.) as well as pumping capability which would enable the stopping or starting of flows, changing flow rates, and varying which flow cells are addressed by a particular liquid. Means to connect external pumps, conduits, valves, and fluid reservoirs may also be provided.

The fluidic manifold 602 may incorporate additional functional elements that permit sensing and monitoring of physical changes in the region. These elements include voids, reference flow cells, lenses, gratings, mirrors, wave guides and/or electrodes. Physical properties sensed may include refractive index, light absorbance, thickness, light scattering, conductivity, electrochemical potential, and pH. Sensing methods may include the use of surface plasmon resonance (SPR) techniques, atomic force microscope (AFM) techniques, ellipsometry, spectrophotometry, nephelometry, multipole coupling microwave spectroscopy, fluorescence, phosphorescence, and chemiluminescence.

The fluidic manifold 602 may be made of a single layer or piece or several layers and/or pieces as needed to best implement the desired flow cells, regions, flow distribution and sensing schemes. The manifold or portions thereof may be made of materials such as cycloolefin co-polymer (COC) and cycloolefin polymer (COP), polydimethyl siloxane (PDMS), silicon, plastics, glass, etc. Surface treatments may be employed within and differently among various flow channels and voids to control such things as adsorption, specific and non-specific binding, hydrophobicity and hydrophilicity.

The manifold may be held against the substrate by mechanical means such as clamps, frames, bezels, springs, flexures, screws, clips, or combinations thereof. Alternately, the manifold may be held against the substrate by properties inherent in the materials of the substrate and the manifold. Yet alternately, the manifold may be held against substrate by an adhesive layer, an adhesive material or adhesive treatment; or by vacuum means; or by a combination of mechanical, adhering, or vacuum means.

FIG. 6A is an unassembled view of a fluidic enabled protein biochip array system according to an embodiment of the present invention. This figures shows the substrate 610 having chemically selective regions 611, the microfluidic manifold 612, a smartcard 614 having a read/write enabled memory device 616 and a two piece bezel 618A, 618B to hold all the parts together. An assembled view of the device 620 is shown in FIG. 6B.

FIG. 6C is a diagram of the substrate 610 and the chemically selective regions 611. In one embodiment, for example the embodiment shown in FIG. 6C, the regions 611 and their relative location on the substrate 610 are chosen to have a dimension of approximately 0.5 to 2 square millimeters or larger, so as to have regions with surface areas that are uniquely sized for LDI sensitivity. The regions 611 may also include a single waveguide grating structure or paired waveguide grating structures.

FIG. 6D is a schematic diagram of an embodiment of the fluidic system of the present invention. This diagram describes an embodiment of the fluidic system for the processing of the substrate of FIG. 6C. It should be realized that this diagram is exemplary and not meant to limit the scope of the present invention. In addition to cells 650 A–F that correspond to the regions 611, this diagram shows that each cell is placed in-between valves 652A–F and check valves 654A–F that are used to regulate the flow of fluids into and out of the cells 650A–F from various sources using various channels, as is shown in the FIG. 6D.

As is shown, the glass substrate includes six independent sensing sites. Each sensing site has one in-coupling grating and out-coupling grating. The choice of having six sensing sites is completely arbitrary, as each sensing site is separately addressable and monitorable. In one implementation, a substrate having six sensing sites is illuminated by a tunable laser delivering a single wavelength of light to generate out-coupled light from six output gratings where the light out-coupled from each sensing site is detected by its own dedicated one of six detectors. The detected distribution of each individual site is processed individually to identify the wavelength of maximum coupling. Systems with 24–100 individually addressable sensing sites are currently envisioned.

Although an array of sensing pads is shown on the glass substrate, each sensing pad is individually addressable. Each of the sensing pads receives light having the same one wavelength. And the out-coupled light emitted from each sensing site is detected by its own dedicated detector.

FIG. 6F is an operational diagram of one of the sensing pads. The setup shows a glass substrate with a waveguiding layer and having one sensing pad having one in-coupling grating and an out-coupled grating.

In an alternate embodiment, the glass substrate is coupled with a fluidic system as is described below, in conjunction with FIG. 6H. FIG. 6H is an exploded assembly diagram of an alternate fluidic enabled protein biochip array system according to an embodiment of the present invention. All dimensions shown in FIGS. 6H–6O are exemplary and are not meant to limit the scope of the present invention. A credit card-sized carrier 1612, having frame 1614 thereon, receives the substrate 1616. A gasket 1617 sits above the substrate. Two manifold plates 1618 and 1620 are disposed above the gasket. The assembly is held in proper geometric alignment by way of the frame 1614 and parallel pin(s) 1622. The assembled device is coupled with a fluid delivery device, such as for example a syringe 1624 for delivery of fluid to and from the substrate 1616 via ports 1626 (10 ports are shown in the figure). In one embodiment, the assembly is an integrated fluidic system for protein analysis. The disposable part will consist of a multi-layer micro-channel plate with 6 cells for protein samples. This plate serves as a removable lid for a glass slide, which is the carrier for the protein samples. Further details of the system are provided below.

FIG. 6I is an exemplary schematic of the fluidic system layout of FIG. 6H. The schematic layout fulfils the requirement regarding flexibility of chemical analysis as wells as the feasibility of production. It consists of 2×5 ports (A–J) 1626, 14 pressure controlled active membrane valves (normally open) 1628, two central stations 1630A and 1630B and 8 open waste ports 1631. The regions on the substrate that are wetted by the fluidic system are shown as cells (1–6) 1632.

The system allows the independent addressing of every cell and a simultaneous or parallel filling of several cells. The two central stations reduce the complexity of interconnections. They permit the flow of two different fluids simultaneously permitting parallel experiments to be performed. Both central stations can be flushed separately or parallel. Each of the assembly parts are described further below. The credit card-sized carrier consists of a standard credit card format card with a cut out for the frame. An exemplary syringe is provided by the Hamilton Company. The glass substrate with a feature layer is as described above and fits into the frame. It is fixed in place by using a combination of fix points and flexible points to approach an accurate position. Separation from frame is enabled by moving the retention tabs using a pointed tool. The frame is made by metal or reinforced polymer. The task of the frame is to position and fasten the other parts. In particular, the frame: locates and fastens the substrate to card; fastens the fluidic system to the substrate and is removable to provide direct access to features, e.g. for LDI MS; includes features to provide location of the substrate and the fluidic system in a scanning device; allows optical interrogation of the substrate; and provides enough force to prevent leakage across the surface of the substrate when not running. The scanner device supplies additional clamping force to hold off up to 2 bar when running.

FIG. 6J is a drawing of various details of FIG. 6H. A perspective view shows the syringe 1624 coupled with a port 1626 of the top portion of the fluidic system 1620. The top portion 1620 is held in place against a carrier 1612 by the frame 1614. In addition, the top view shows that alignment holes 1634 are used to receive pins to hold the pieces in proper alignment against one-another. Section A—A provides a sectional view which aids in describing the assembled device. As is shown in section A—A, a credit card carrier 1612, receives the substrate 1616. Above the substrate is located a first manifold plate 1618. This plate contains channels, valves, as well as localization holes (see FIG. 6L for further details). A valve membrane 1636 is located between the first manifold plate 1618 and the second manifold plate 1620. The valve membrane (see FIG. 6N for further details) is used to operate all valve functions. It is clamped between the manifold plates and also seals the valve areas. The second manifold plate consists of the ports for the syringes, the cavity for the valve membrane, the holes for valve control and localization holes (see FIG. 6K for further details). Detail B shows a gasket 1638 placed between the substrate and the first manifold plate. Frame 1614 holds the pieces together on the carrier card and pin 1622 provides for the relative positioning and fit of the component parts.

Also shown are the gas inlet ports 1640 (14 are shown) that are used to control the flow of fluids through the valves. Detail D of section view C—C shows one gas inlet port 1640 which is used to seat the valve membrane against the fluid inlet 1642 and Outlet 1644 for each valve.

FIG. 6K is a detailed drawing of the second manifold plate of FIG. 6J. The second manifold plate consists of the ports for the syringes, the cavity for the valve membrane, the holes for valve control and localization holes. A perspective view of the second manifold plate aids in the description of this plate. Three additional views provide a top, a side and a bottom view of the plate. The top view shows the syringe inlet ports (10 are shown) 1626 surrounding the pneumatic pathways 1640 to seal the diaphragm to close the valves. The bottom view shows a recess 1646 to receive the valve diaphragm.

FIG. 6L is a detailed drawing of the first manifold plate of FIG. 6J. A perspective view of the first manifold plate aids in the description of this plate. Three additional views provide a top, a side and a bottom view of the plate This plate is the microstructured plate which consists the micro channels 1650, micro valves 1652 as well as localization holes 1634. Central stations 1630A and 1630 B are also shown, as are waste ports 1653. The integrated valves are pressure controlled membrane valves which are normally open. The pneumatic pressure pushes the membrane into a cavity and disconnect the attached holes at the ends. A maximum pressure for actuation is 2 bars.

FIG. 6M is a detailed drawing of the frame 1614 of FIG. 6J.

Figure 6N:
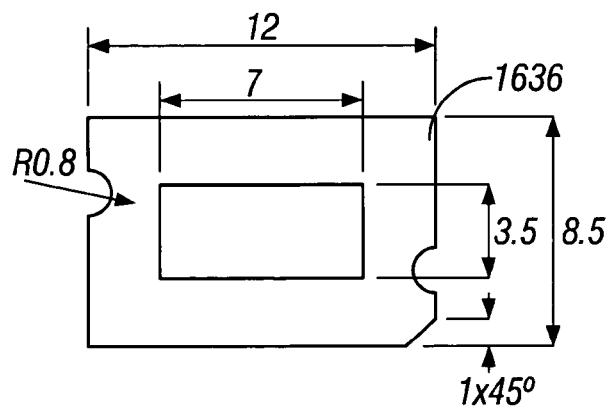
FIG. 6N is a detailed drawing of the valve membrane of 6J.

FIG. 6N is a detailed drawing of the valve membrane 1636 of 6J. The valve membrane is used to operate all valve functions. It is clamped between the manifold plates and also seals the valve areas.

Figure 6O:
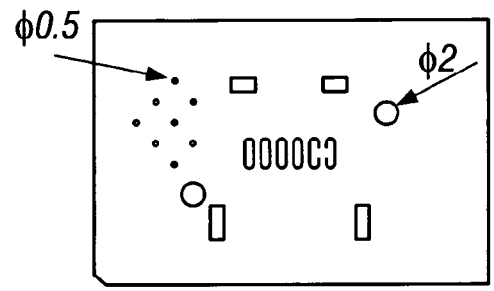
FIG. 6O is a detailed drawing of the gasket of 6J.
Figure 7:
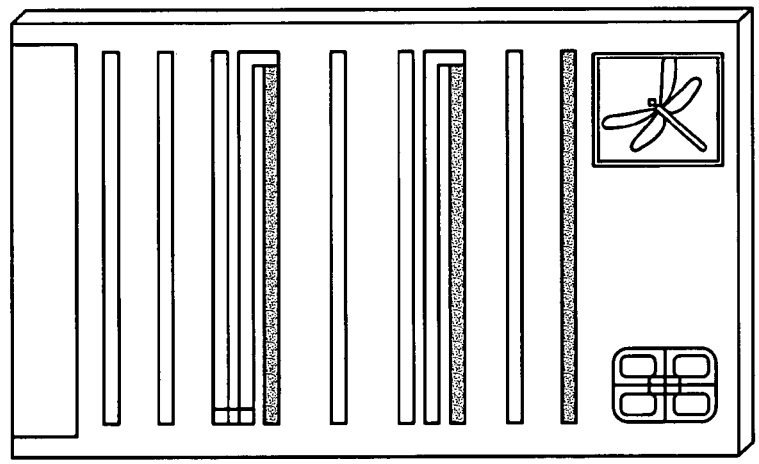
FIG. 7 is a diagram of a protein biochip planar chromatography array system.

FIG. 6O is a detailed drawing of the gasket 1638 of 6J. The gasket and the membrane are made of an elastic material such as for example, silicone rubber or Santoprene. The gasket, preferably with a thickness of between 50 and 100 µm consists of cavities which define cell volume and which seals the manifold channels.

The microfluidic enabled chip array in accordance with embodiments of the present invention is advantageous over currently available bio or protein biochip arrays for reasons set forth below.

As set forth above, currently available protein biochip arrays are processed in a series of steps that includes application of various fluids to the regions. The entire chip can be processed with a single fluid by immersion or rinsing of the entire chip. To effect processing of individual regions on a chip, fluids are applied in aliquots that are small enough to be retained over a region by their own surface tension, or held in place over the region in a small open top vessel formed by walls and having the region as a floor.

In the case where the fluids are held in place over a region by their surface tension, the areas of the chip outside of the regions are made hydrophobic so as to repel the fluids and keep them on the regions. Application of the aliquots is done by hand using a pipette. The application of the aliquots may also be carried out by a robotic device (506 in FIG. 5) for a high-throughput system. Further processing may include incubation (e.g., deferring further processing or analysis for a definite period of time), heating, cooling, agitation, and so on. It is often necessary or desirable to remove one fluid prior to applying the subsequent fluids or to wash a feature by repeatedly adding and removing a washing fluid. This processing may be difficult and time consuming. One disadvantage of this conventional approach is that during the processing of a chip by this method, there is ample opportunity for cross contamination. Furthermore, during conventional processing, tasks are completed in discrete steps with no monitoring. Therefore, there is no opportunity to vary the processing during each step in response to any monitoring.

In addition to the aforementioned advantages, the use of a fluidic manifold obviates the manufacturing requirements to make discrete locations for the arrays in a manner that is currently employed. Consequently, bulk solution synthesis may be used, circumventing the use of expensive and complicated robotics to generate the discrete locations on the chip. Also, the need for applying a hydrophobic feature creating coating to these arrays is eliminated.

In embodiments of the present invention, the regions form the floor of a flow cell or region and fluids are applied to the regions by flowing them through conduits in the fluid manifold. The voids that form the flow cells also define the feature area such that there is no need to make areas of the chip hydrophobic for the purposes of defining the regions. Using a microfluidic-enabled device, the conduits and paths are designed to eliminate cross contamination. A flow can be established through a flow cell permitting fluids to be applied then washed out by the flow of a subsequent fluid. In addition, as set forth above, the fluidic manifold, by incorporating additional functional elements that permit the sensing and monitoring of the physical changes of the regions, enables the real-time monitoring of the regions as they are being processed. Real-time monitoring, including time-dependent monitoring, includes monitoring real-time changes of the sample composition of the analyte and samples as they are processed through the device, which in turn enables the collection of reaction rates and kinetic data for the samples that are being processed by the device. Monitoring of the region allows assessment of the progress or efficacy of each step. Flows may be stopped, started, switched; flow rates can be changed and processing steps changed in response to determinations made by the monitoring to achieve better and/or faster results.

Chip processing steps that would be amenable to the technique of using a novel combination of a fluidic manifold and a protein biochip array include: the preparation of the region surfaces; chemical preparation of surfaces with the fluidic manifold; introduction of analyte, reagents and washes to and/or through the flow cells; application of matrix solutions to the regions; drying of the SELDI matrix; application of proteolytic agents to support protein ID activities, as well as many others.

In addition to the chip processing techniques described above, the embodiments of the novel integrated fluidic system and bio (or protein) chip array described above, enable a process for detecting an analyte. The process includes: providing a substrate having a chemically selective surface, where the substrate is attached to a fluidic system; delivering a sample comprising an analyte using the fluidic system to at least one sample region on the substrate; monitoring physicochemical changes of the surface in response to the analyte; removing a portion of the fluidic system to render a portion of the surface directly interrogatable by a surface based analytical technique; and detecting physicochemical changes of the surface region. The method may also include interrogating the surface after the removal of a portion s of the fluidic system using LDI-MS.

The substrate with the chemically selective surface can include a chemically selective surface having a reactive moiety and the sample region includes a capture reagent that is bound by the reactive moiety. The capture reagent may be bound by the moiety by physi-sorption. The process may also include delivering a conditioning fluid to the surface after the delivering the sample. The process may also include delivering a reagent to selectively functionalize the surface after delivering the sample. The process may also include delivering the sample to several discrete locations on the surface.

The sample that is delivered can be one of several samples and the sample region can be one of several different sample regions and then the delivering can include delivering each of the several samples to the different sample regions. When the setup is used for LDI-MS, the fluidic system may be used to deliver a matrix solution to the sample region before directing energy at the sample region.

One method of the invention takes advantage of the ability to move fluids from one discrete location to another by directing fluid along selected fluid paths. For example, one can direct an analyte to one feature for capture and an affinity capture measurement. Then, fluid containing a reagent, such as a protease, can be directed to the feature to react with the captured analyte. The modified analyte can be detected in place or fluid can be directed over the feature to transport products of the reaction to a second feature where they can be analyzed by the methods of this invention.

C. Detection at the Chip Surface without Direct Physical Communication

As set forth above, interrogation without physical communication includes SPR and techniques using diffraction grating coupled waveguides, such as WIOS. Both of these interrogation techniques are carried out while the fluidic system is in place and disposed on the substrate. These non-contact techniques enable the real time interrogation of the biochip surface while the fluidic system is in place.

An embodiment of a surface scanner arrangement for interrogating the fluidic coupled substrate is shown in FIG. 6E. As is shown in this figure, a laser source 1602 delivering laser light is used to illuminate a substrate 1604 containing an array of matched input and output grating structures. Each sensing site includes one input grating and one output grating. An optical setup including a lens 1606 used to form a collimated laser light that is large enough to illuminate the array of sensing sites. The out-coupled light from each sensing site is then detected by a detector 1608. There is one detector for each one out-coupled light from each sensing site. The output of the detector is further processed to identify the wavelength of maximum coupling or intensity as shown in FIG. 6G.

Shown in FIG. 6F is an analyte layer 1610 covering the top of the substrate. Laser light is collimated and directed at the one in-coupling grating of the one sensing pad, the out-coupled light is directed to a detector via an optical fiber bundle and the detector is used to process the detected light to identify the wavelength of maximum intensity (FIG. 6G). In one embodiment, the processing of the detected signal provides a measure of the location (e.g., in wavelength units) of the maximum intensity as shown in FIG. 6G. This processing is advantages over other techniques, (e.g. position and/or intensity) because by detecting the wavelength of the maximum intensity, the measurements are inherently independent of the actual or absolute value of the intensity; the detector is used to detect the wavelength of maximum intensity regardless what the position or the value of that intensity is. The detector detects the relative maximum of intensity and identifies the wavelength that produces that maximum intensity. The one detector sees only the light emitted from the one sensing pad, and the generated signal is produced by the processing of the detected.

In addition to the optical monitoring, the monitoring of the physicochemical changes of the surface includes electrochemical monitoring, atomic force monitoring, a radio frequency monitoring, a piezoelectric vibrating member monitoring, a resonate cantilever device monitoring, and combinations of these. The optical-based monitoring is configured to monitor changes in properties of polarization of light caused by interaction of light with the surface. The properties that are monitored include fluorescence, luminescence, chemiluminescence, absorbance, reflectance, transmittance, birefringence, refractive index and combinations thereof.

The optical monitoring may include using an optical-based device that is configured to detect changes in the refractive index at the surface, such as for example, a grating coupler waveguide device. The grating coupler waveguide device is interrogated by varying the wavelength of incident radiation at a fixed angle and determining the wavelength of maximum coupling. Alternately, the grating coupler waveguide device is interrogated by varying the angle of the incident light of a fixed wavelength and determining the angle of maximum coupling. Yet alternately, the grating coupler waveguide device is interrogated by illuminating the grating coupler device with light having a range of wavelengths and determining the wavelength of maximum coupling by measuring the wavelength of the coupled light. Or, the grating coupler waveguide device is interrogated by illuminating the grating coupler device with light of a fixed wavelength over a range of angles and determining the angle of the coupled light. Or, the grating coupler waveguide device is interrogated by one of the following: varying the wavelength of incident radiation at a fixed angle and determining the wavelength of maximum coupling, varying the angle of the incident light of a fixed wavelength and determining the angle of maximum coupling, illuminating the grating coupler device with light having a range of wavelengths and determining the wavelength of maximum coupling by measuring the wavelength of the coupled light, and illuminating the grating coupler device with light of a fixed wavelength over a range of angles and determining the angle of the coupled light.

Alternately, the monitoring is an electrochemical monitoring and the structures include electrodes in electrical communication with said surface. Yet alternately, the monitoring is performed using an atomic force microscope (AFM) and the structures include AFM probe or port for accepting an AFM probe in physical communication with the surface.

Alternately, the monitoring includes using a radio frequency device and the structures include a radiofrequency waveguide in radio frequency communication with the surface.

The process for detecting an analyte can also include providing a substrate that includes structures for rendering the substrate compatible with a device for monitoring physiocochemical changes of the surface. The monitoring includes an optical monitoring and the structures include an optically transmissive path communicating with the surface. The path can be a window, a lens, a prism, a surface planar waveguide or an optical fiber. Alternately, the monitoring includes an optical monitoring and the structures can include a polarizer, a lens, a mirror, a diffraction grating, a wave plate, an attenuator, an interferometer and combinations thereof.

D. Detection with Surface-Based Analytical Tool

As set forth above, detection with a surface-based tool involves the removal of the fluidic system, or a portion thereof. Examples of surface-based tools include a mass spectrometer. With the fluidic system (or a portion) removed, the substrate is supported by its carrier which is adapted to interface with a probe interface of a mass spectrometer. The interaction between the analyte and the capture molecule is detected using the mass spectrometer, using known techniques.

Furthermore, the process for detecting an analyte may also include the prior electrophoresis of the sample, the electrophoresis including capillary denaturing, nascent, free zone, isoelectric focusing, isotachophoresis, gel electrophoresis, or combinations thereof. In addition the process for detecting an analyte includes: providing a device having a substrate and a fluidic manifold disposed on the substrate, where the device includes an electrophoresis medium on the substrate surface; electrophoresing a sample including analytes through the medium, such that the analytes are electrophoretically separated through the medium; detecting in real-time the electroporesis of the sample by a surface scanner; and; further detecting the separated analytes by laser desorption/ionization mass spectrometry.

E. System

The processes described above can be carried out in system as described below. Such a system includes a device having a substrate and a fluidic system; and devices for interrogating the substrate surface when the fluidic system portion is coupled with the device. In connection with the device, the substrate has a chemically selective surface and the fluidic system is disposed on the substrate. The fluidic system includes: at least one fluid path in communication with at least a discrete region of the surface, such that the one fluid path and the discrete region together define a contained sample region on the surface. The fluidic system includes a removable fluidic system portion. As described above, the device also includes structures for fastening the fluidic system to the substrate; structures for engaging a first detection system, such that the device is removably insertable into the detection system; and where the first detection system includes structures for interrogating the substrate surface when the fluidic system portion is integrated with the device. The device also includes structures for engaging a surface-based analytical tool, where the surface-based analytical tool functions by interrogating the substrate surface as a result of removal of the fluidic system portion.

In one embodiment, the structures for interrogating include an optical device and the structures for engaging include an optically transmissive path communicating with the surface, where the path may be a window, a lens, a prism, a surface planar waveguide or a fiber optic.

The optical device is configured to monitor changes in properties of the polarization of light caused by interaction of light with the surface. Alternately, the optical device is configured to monitor properties of the surface, which can include fluorescence, luminescence, chemiluminescence, absorbance, reflectance, transmittance, birefringence, refractive index and combinations thereof.

Alternately, the optical device is configured to detect changes in the refractive index at the surface.

In one embodiment, the substrate includes a grating coupler waveguide. In one aspect, the waveguide is interrogated by varying the wavelength of incident radiation at a fixed angle and determining the wavelength of maximum coupling. Or, the waveguide is interrogated by varying the angle of the incident light of a fixed wavelength and determining the angle of maximum coupling. Or, the waveguide is interrogated by illuminating the grating coupler device with light having a range of wavelengths and determining the wavelength of maximum coupling by measuring the wavelength of the coupled light. Or, the waveguide is interrogated by illuminating the grating coupler device with light of a fixed wavelength over a range of angles and determining the angle of the coupled light. Or, the waveguide is interrogate by a combination of these interrogation techniques.

In one embodiment of the system described above, the device for interrogating includes an optical device and the means for engaging the device can include a polarizer, a lens, a mirror, a diffraction grating, a diffractive element, a wave plate, an attenuator, an interferometer and combinations thereof.

Alternately, the device for interrogating includes an electrochemical device and the means for engaging the device includes electrodes in electrical communication with the surface. Yet alternately, the device for interrogating includes a radio frequency device and the means for engaging the device include a radiofrequency waveguide in radio frequency communication with the surface.

F. Application of MALDI MS Matrix to Protein Biochip Arrays via a Fluidic Manifold Another embodiment of the present invention is directed towards a novel application of MALDI MS Matrix to a protein biochip array (e.g., a SELDI/ProteinChip® Array) via a fluidic manifold. In this embodiment of the present invention, MALDI MS matrix solution is introduced, via conduits in the manifold, onto lanes and regions on the chip that will subsequently be probed using SELDI MS. Analytes of interest adsorbed on the lanes and regions desorb into the matrix solution. The solution is then crystallized in situ by application of a vacuum or flow of dry gas through the manifold. The manifold, or a portion thereof, is removed to uncover the crystals and allow SELDI MS to be performed on them.

The surfaces of the manifold forming the voids over the lanes or regions may be caused to be hydrophobic so as to cause the matrix to crystallize preferentially on the chip surface. In this case, SELDI MS is performed on the crystals adhered to the chip surface. Alternatively, the surfaces of the manifold may be treated to cause the matrix to crystallize preferentially on the manifold surfaces. In this case SELDI MS is performed on the crystals adhered to the fluidic manifold.

Access to the crystals for the purpose of performing SELDI MS may be gained by separating the manifold from the chip and thereby exposing the crystals either on the surface of the chip or the surfaces of the manifold. Alternatively, the manifold may be constructed of separable layers or have caps or plugs over the lanes or regions, such as for example, chromatographic lanes and regions such that one or more layers is removed or the plugs or caps are removed to provide access to the crystals.

This embodiment of the present invention provides for many advantages over current methods and systems that process ProteinChip® arrays. In currently available systems, SELDI/ProteinChip® Arrays are prepared for MS analysis by applying aliquots of matrix solution, which is retained over a region by selective surface tension. The area of the chip outside of the regions is made hydrophobic so as to repel the aliquots of matrix solution and keep them on the lanes or regions. Application of the aliquots is done by hand using a pipette, or alternately by using a robot. The aliquot must remain in liquid phase long enough for the analytes to be desorbed from the surface and released into the overlying solution phase. Under some low humidity or high temperature ambient conditions or when using small volumes of matrix solution, it is necessary to provide a humid environment for the chip to prevent the matrix solution from crystallizing before the analytes can desorb into the matrix solution. During this process, there are many opportunities for extraneous contamination from ambient pollutants (e.g., air borne proteins, etc.).

Using the embodiments of the present invention, the matrix solution is applied via a fluidic manifold that, generally, will have already been applied to the chip and used for performing chip processing steps prior to the application of the matrix solution. In this case, application of the matrix solution is integral with the chip processing system so no separate handling or separate equipment is needed to apply the matrix solution. The matrix solution is contained in the voids in the manifold so there is no need to make areas of the chip surface hydrophobic for the purposes retaining the matrix solution over lanes or regions. Also, the matrix solution will remain liquid until caused to crystallize by the application of vacuum or flow of dry gas. Because the matrix solution is contained in the voids, opportunity for contamination or cross contaminations is greatly reduced.

An alternate embodiment of the present invention, introduces the matrix solutions via the fluidic manifold then removes the separable layers, plugs or caps, while the matrix solution is still in liquid form. Crystallization would then occur through evaporation into the ambient environment.

G. Chromatography on Protein Biochip Arrays

Another embodiment of the present invention is directed towards a novel device and method for performing chromatography on a protein biochip array, such as, for example, SELDI/ProteinChip® Arrays. For this embodiment, a fluidic manifold is applied to a SELDI/ProteinChip® array. The manifold contains channels that define lanes 702 on the surface of the chip 700. These lanes 702 can be prepared with a chromatographic stationary phase so as to function as thin layer chromatographic surfaces. Alternatively, a channel above the lane may be filled with a chromatographic stationary phase, or function as an chromatographic column. A volume of suitable solvent is caused to flow through the channels and over the lanes. A bolus of sample mixture is introduced into that flow prior to the lane in the manner typically done in liquid chromatography. With suitable choice of solvent, flow rate, and stationary phase, a separation of the sample mixture into its constituent components can be effected. The flow can continue and the constituents be allowed to elute off the stationary phase for capture or later processing; or the flow can be stopped and the separated constituents retained on the stationary phase as in retentate chromatography.

The fluidic manifold and chip may have a plurality of lanes with same or different dimensions or same or different stationary phases. A single sample mixture may be applied to several lanes, different sample mixtures may be applied to different lanes, and lanes may be arranged such that a sample mixture can flow through several lanes in succession.

In addition to lanes, the fluidic manifold and chip may include flow cells and regions for further processing or affinity capture of the sample mixtures and/or constituents. The fluidic manifold and chip may also include lanes, channels or conduits in which packed column or capillary chromatography is performed.

When performing chromatography on the chip array, the sample region may have a thin-layer chromatographic surface and the process includes flowing the sample across the chromatographic surface, and chromatographically separating the analyte in the sample region. The chromatographic separation may be a Reverse Phase, ion exchange, mixed mode, normal phase, immobilized metal affinity capture, affinity capture, and combinations thereof. The chromatographic separation includes monitoring the chromatographic surface at various locations; and detecting analytes bound to the capture reagent at the locations.

Figure 8:
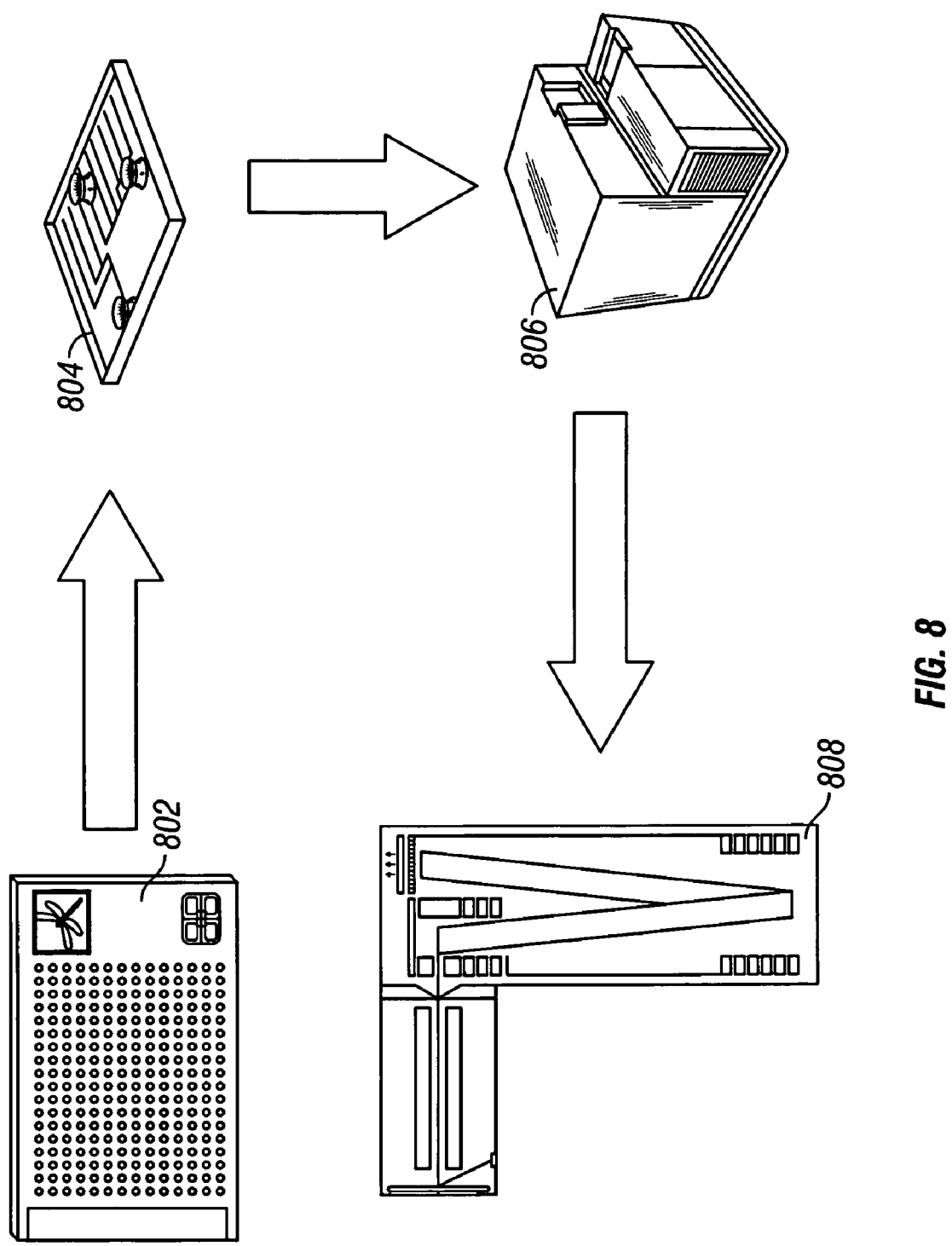
FIG. 8 is a diagram of various novel modules used for the processing protein biochip arrays.

As shown in FIG. 8, the embodiments of the method and device of the present invention, combine a protein biochip array 802, with a fluidic manifold 804 and process the device using the manifold as well as other devices. During the process of separation, an instrument(s) can be employed that would monitor the surface and detect the presence of sample mixtures or their constituents at various places on the chip including in the lanes, in conduits, or on affinity capture surfaces. Physical properties sensed can include changes in the refractive index, light absorbance, thickness of adsorbed layers, light scattering, conductivity, electrochemical potential, and pH. Sensing methods could include grating coupler waveguide detection, SPR, AFM, ellipsometry, spectrophotometry, nephelometry, multipole coupling microwave spectroscopy, interferometry, fluorescence, phosphorescence, and chemiluminescence. Many of these instruments are shown collectively as a surface scanner 806 in FIG. 8.

After a chromatographic separation is effected, matrix solution could be applied and SELDI MS 808 could be performed on areas of interest on the chip, including the lanes and chemically selective surfaces.

This embodiment of the present invention provides for many advantages over current methods and systems that process protein biochip arrays. For example, currently available SELDI/ProteinChip® Arrays are processed in a series of steps that includes application of various fluids to the regions. To effect processing of individual regions on a chip, fluids are applied in aliquots retained over a region by their own surface tension or held in place over the region in a small open top vessel formed by walls and having the region as a floor. Performing chromatography in this way, by adding aliquots over chromatographic stationary phases and subsequently washing the surface separations, can only effect separation between constituents of a sample mixture that have greatly different retention by the stationary phase.

As enabled by the embodiments of the present invention, using flowing liquids along a chromatographic bed will yield all the well-known benefits of the method and make them integral with the preparation and processing of SELDI/ProteinChip® processing. In essence, current retentate chromatography approaches rely upon solid phase extraction, which is limited to a single theoretical plate of chromatographic efficiency. The embodiments of the current invention, employ a true chromatographic approach, approaching 1000 theoretical plates. The overall improvement to chromatographic resolution is depicted by the following expression:

$$R_{(improvement)} = N^{1/2}{}_{(planar\ chromatography)}$$

Consequently, when compared to current retentate chromatography methodologies, planar chromatography can improve chromatographic resolution by as much as 32 times.

H. Chemical Sample Storage with Integrated Memory Capability

Another embodiment of the present invention is directed towards a device, such as a chemical sample storage device having an integrated read/write memory capability. As is generally known, chemical samples are processed, analyzed, and/or stored in a holder. The holder may be a single reservoir, such as a vial, or array of reservoirs, such as a micro titer plate. In other cases it may be a plate or chip on which chemical samples may be stored, analyzed, and/or processed such as a DNA chip or ProteinChip® array in accordance with embodiments of the present invention.

Figure 9:
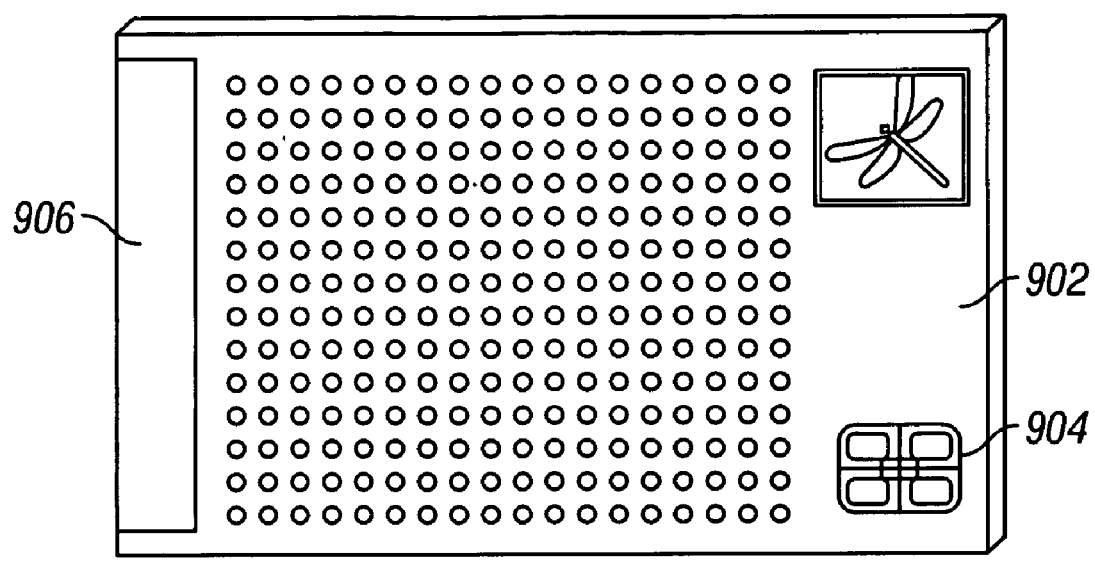
FIG. 9 is a diagram of a novel protein biochip array having an integral memory device.

The array 902 includes a data memory device 904 (shown in FIG. 9) such as a magnetic stripe or electronic memory. Records can be written to the memory device and can be read from the memory device. Reading or writing records to and from the memory device may be done via magnetic means, optical means, via electrical connections, via radio frequency, or by other means. Reading can be accomplished via means that physically contact the array, are in close proximity to the array, or are located remotely from the array. Records may be written or stored in the memory device in secure manner so that only authorized individuals or authorized devices may read and/or write the data. Additionally, the array 902 may include means facilitating the use of a surface based analytical technique to enable the in-situ monitoring of the array using a surface scanner.

Records may include: the type and/or identity of array; the type and/or identity of chemical samples in the array; the types and/or identities of the source of the sample; a record of processing or analysis to which the array or chemical samples have been subjected including: location, date, time, conditions, specific equipment, operators, calibrations, and so on; data and/or results of processing and/or analysis; instructions and/or limitations for processing, handling or analysis; and other information associated with the array, chemical samples, processing, analysis, etc.

The memory-device-enabled novel device of the present invention provides many advantages over currently available devices. Currently, arrays are often provided with panels or labels on which information can be recorded. Only a very limited amount of information can be recorded in the form of text on such a panel or label, whether written by hand, typewriter, or printed by a computer. Typically, more extensive records or data associated with an array or chemical samples are kept separately by hand in a notebook or reside in a machine such as a computer. Text records generally must be read by a technician or operator and entered into notebook or machine.

On the other hand, barcodes provide for labeling a sample with a machine-readable identity but no capability is provided for storing of records associated with the sample or chemical samples. The records and/or data are stored in a machine and associated with the array or chemical samples by the bar-coded identity of the array.

In either of the two cases described above, if the array is to be transported between physical locations or transported between storage areas, lab areas, work areas, processing equipment or analyzing instruments, the records must be separately tracked and transported as needed. If the array and/or chemical samples are to be subject to a series of processing or analyzing steps the records necessary in order to carry out each step must travel with the array and the necessary information transferred to the individuals, equipment, or instruments that will work with the array and or chemical samples. In larger labs, this is made easier by the implementation of a laboratory information management system "LIMS" where by all locations or joined in a network and can share information.

In stark contrast, as is embodied by the present invention, the records are stored in a memory device that is a part of the array. Laboratory areas, processing equipment, and instruments are equipped to read and write information to the memory device. Records containing information identified above can be partially or entirely stored in the memo device and, as such, remain associated with and travel with the array and/or chemical samples. No separate effort or system is required to associate records with arrays or chemical samples or to keep records located with the arrays.

I. LDI Pneumatic and Electrostatic Lenses within the Fluidic Manifold

In another embodiment of the present invention a portion of the fluidic manifold is removable as to expose each region for direct LDI analysis, where each region contains electrostatic elements, such as conductive plates cones, and/or pneumatic elements, such as passageways or apertures that direct the movement of desorbed ions, that facilitate the collection and transmission of LDI created ions. Certain features of this particular embodiment include: integral pneumatic channels to allow for pneumatic entrainment and transmission of desorbed ions; integral electrodes which allow for the application of RF or dc electrostatic fields to facilitate ion collection and transmission into down-stream MS systems.

J. Disposable Positive Displacement Micro-Syringe for Fluid Introduction and Pumping on Biochip Arrays Another embodiment of the present invention is directed towards a disposable positive displacement microsyringe for fluid introduction and movement on biochip arrays. As describe above, a novel biochip array in accordance with embodiments of the present invention includes a chemically selective surface(s) with a fluidic manifold disposed over the surface to define sample regions on the chemically selective surface(s) and provide for the flow of liquids and or gasses to and over the surfaces. In use, multiple fluids must be introduced and/or caused to flow into and/or over chemically selective surfaces, and/or over or through chromatographic surfaces or channels within the manifold.

This embodiment of the present invention is directed to using a small, disposable, positive-displacement syringe(s) (one or more) to take up volumes of fluids from repositories such as wells in a microplate, move the syringes to the chip, insert the tips of the syringes into a receptacles in a fluidic manifold on the chip achieving a fluid(gas)-tight seal, and use actuators to move the pistons of the syringes to cause a known amounts or flow rates of the fluids to enter and/or pass through the chip. Similarly, the syringes may also be used to draw fluids or gasses through the chip.

If several fluids are to be introduces into a single fluidic network on the chip, each syringe would serve to seal its respective receptacle, preventing flow from other syringes from exiting from that receptacle.

Figure 10:
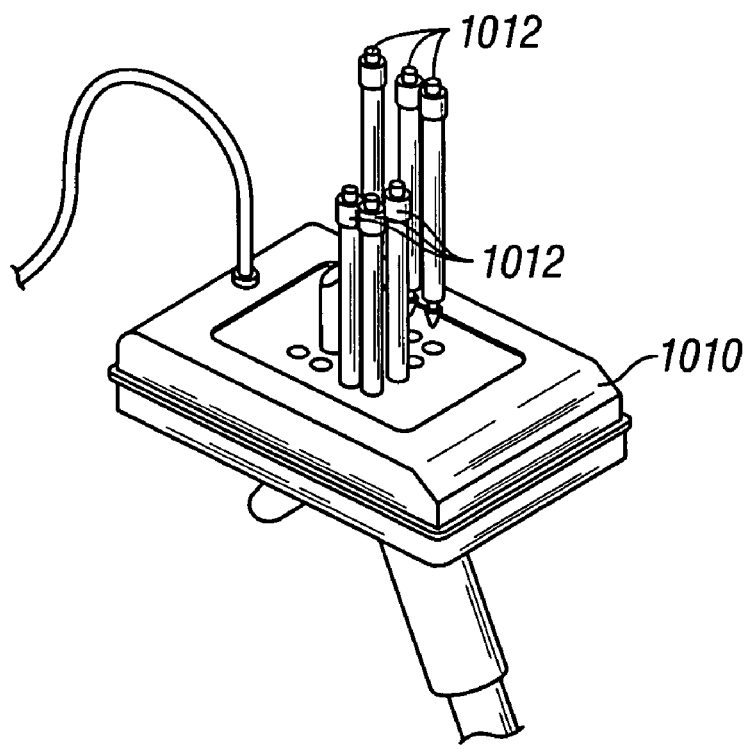
FIG. 10 is a diagram of the chip of FIG. 6B clamped in a temperature regulated block and showing the microsyringes mating with the block.

For some applications of biochip arrays, control of the temperature of the biochip and fluids is desirable. As is shown in FIG. 10, the syringes 1012 can be arranged such that the fluid-containing portion makes intimate contact with a bore in a thermally conductive block 1010 or enclosure, the block or enclosure disposed over and/or around the biochip for the purpose of controlling or maintaining its temperature, while the syringes are inserted into the receptacle in the fluidic manifold. This enables the fluid to rapidly come to the same temperature as the block and chip. The use of the microsyringes is advantageous because they are inexpensive and can be disposed of after each use and they also greatly reduce the opportunity for cross contamination. In these ways, the syringes serve to pump and control the sequence and flow rates of the various liquids into and through the biochip.

The microsyringe-enabled embodiment in accordance with embodiments of the present invention provides for many advantages over current methods and systems that are used to process biochips. One way prior fluid delivery is by using pipettes. Because pipettes generally use disposable tips, they have the advantage of minimizing cross contamination. Pipettes have the disadvantage of having a relatively large volume of gas between the displacement piston and the fluids. The compressibility of this gas makes it difficult to control the amount of fluid delivered or flow rates of fluids when there is significant and/or varying resistance to flow in and among fluidic manifolds. It is also difficult to achieve adequate pressure to overcome resistance to flow in the fluidic manifold and through chromatographic channels. The microsyringe embodiment of the present invention has a very little, if any air between the piston and the fluid so consistent accurate volumes of fluid can be deliver or accurate flow rates achieved even with the higher resistance to flow encountered in some chromatographic channels.

Another way prior art accomplishes the above is by conducting the fluids to the chip through tubing (including channels) and fittings, moving fluids through the tubing by various pumping means and controlling fluids flow using valves, injection loops, etc. Temperature regulation of the fluids is achieved by regulating the entire external fluidic system (reservoirs, tubing, valves,) and/or employing heat exchangers in thermal contact with, or regulated to the same temperature as, the biochip, through which the fluids flow. The advantage of this type of system is that it can achieve the consistent flow volumes and rates as well as overcome resistance to flow encountered in fluidic manifolds or chromatographic channels therein. This system has the distinct disadvantage of allowing cross contamination between subsequent samples unless all wetted surfaces are disposed of between samples or extensive flushing is performed. This is particularly troublesome when attempting to perform assays with sticky biomolecules like proteins. Further, the large wetted areas involved will deplete analytes such as proteins from fluids through nonspecific binding to the surfaces. This can affect analytical accuracy and performance as well as be costly because of the loss of high cost, precious or rare analytes. The microsyringe embodiments of the present invention suffers from none of these shortcomings.

In another embodiment of the invention an experiment can be performed on an analyte in the device and then microsyringes can be used to extract fluid from the location to move it to an external reservoir or to another location on the biochip for further processing.

II. Data Generation in Mass Spectroscopy

Data generation in mass spectrometry begins with the detection of ions by an ion detector. Ions that strike the detector generate an electric potential that is digitized by a high speed time-array recording device that digitally captures the analog signal. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

Analysis generally involves the identification of peaks in the spectrum that represent signal from an analyte. Peak selection can, of course, be done by eye. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated while employing the embodiments of the invention can be classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

In some embodiments, data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are in U.S. Provisional Patent Application Nos. 60/249,835, filed on Nov. 16, 2000, and 60/254,746, filed on Dec. 11, 2000, and U.S. Non-Provisional patent application Ser. No. 09/999,081, filed Nov. 15, 2001, and Ser. No. 10/084,587, filed on Feb. 25, 2002. All of these U.S. Provisional and Non Provisional Patent Applications are herein incorporated by reference in their entirety for all purposes.

Alternately, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

Having defined and described several technical terms and mass spectroscopy devices, the embodiments of the present invention that are directed to a novel device and method for identifying an analyte are described below.

III. Definitions

Unless defined otherwise, all technical and scientific terms used herein have the meaning commonly understood by a person skilled in the art to which this invention pertains. The following references provide one of skill with a general definition of many terms used in this invention: Singleton et al., Dictionary of Microbiology and Molecular Biology (2d ed., 1994); the Cambridge Dictionary of Science and Technology (Walker ed., 1998); The Glossary of genetics, 5th ed., R. Rieger et al. (eds), Springer Verlag (1991); and Hale and Marham, The Harper Collins Dictionary of Biology (1991). As used herein, the following terms have the meanings ascribed to them unless specified otherwise.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter which can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer which uses laser as a means to desorb, volatilize, and ionize an analyte.

"Tandem mass spectrometer" refers to any mass spectrometer that is capable of performing two successive stages of m/z-based discrimination or measurement of ions, including of ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF—TOF mass spectrometers, Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter which can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionuclides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (I) electrons which ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe").

"Adsorbent" or "capture reagent" refers to any material capable of binding an analyte (e.g., a target polypeptide).

"Adsorption" refers to detectable non-covalent binding of an analyte to an adsorbent or capture reagent.

"Adsorbent surface" refers to a surface to which is bound an adsorbent (also called a "capture reagent" or an "affinity reagent"). An adsorbent is any material capable of binding an analyte (e.g., a target polypeptide or nucleic acid).

"Chemically Selective Surface" refers to a surface specifically created to interact in a physical or chemical manner with an analyte, organic or biological molecule of interest. The reaction of the analyte, organic or biological molecule of interest with the chemically selective surface can be detectable by a surface-based analytical tool ("SBAT").

"Surface-Based Analytical Tool" or SBAT refers to any analytical tool that is capable of monitoring the presence, or interaction of an analyte with or on a surface of a substrate. SBATs include those tool that require a direct physical communication (DBC) with the surface of a substrate, such as for example tools using laser desoprtion. SBATs may also include tools that do not require a direct physical communication (DBC) with the surface of a substrate, such as for example tools that monitor the substrate surface using optical means.

"Chromatographic adsorbent" or a chromatographic stationary phase refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers an adsorbent comprising a biomolecule, e.g., a nucleic acid molecule, a polypeptide, a polysaccharide, a lipid, a steroid or a conjugate of these (e.g., a glycoprotein, a lipoprotein, a glycolipid). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

Surface-Enhanced Neat Desorption or "SEND" is a version of SELDI that involves the use of probes comprising energy absorbing molecules chemically bound to the probe surface. ("SEND probe.") "Energy absorbing molecules" ("EAM") refer to molecules that are capable of absorbing energy from a laser desorption ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. SEND is further described in U.S. Pat. No. 5,719,060 and U.S. patent application 60/408,255, filed Sep. 4, 2002 (Kitagawa, "Monomers And Polymers Having Energy Absorbing Moieties Of Use In Desorption/Ionization Of Analytes").

Surface-Enhanced Photolabile Attachment and Release or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

"Reactive moiety" refers to a chemical moiety that is capable of binding a capture reagent. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. "Reactive surface" refers to a surface to which a reactive moiety is bound.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected, or its influence or interaction detected or measured. The term can refer to a single component or a plurality of components in the sample.

The "complexity" of a sample interacting with a chemically selective surface refers to the number of different biomolecular species that are interacting with the chemically selective surface.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a continuously varying parameter.

"Biochip" refers to a solid substrate having a generally planar surface to which a chemically responsive layer is attached. Frequently, the surface of the biochip comprises a plurality of addressable locations, each of which location has the adsorbent bound there. Biochips can be adapted to engage a probe interface and, therefore, function as probes.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.), Phylos (Lexington, Mass.) and Procognia (Sense Proteomic Limited) (Maidenhead, Berkshire, UK). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001), International publication WO 00/56934 (Englert et al., "Continuous porous matrix arrays," Sep. 28, 2000), United States patent publication US 2003/0180957 A1 (Koopman et al., "Target and method," Sep. 25, 2003) and United States patent publication US 2003/0173513 A1 (Koopman et al., "Probe for mass spectrometry," Sep. 18, 2003).

Protein biochips produced by Ciphergen Biosystems comprise surfaces having chromatographic or biospecific adsorbents attached thereto at addressable locations. Ciphergen ProteinChip® arrays include NP20, H4, H50, SAX-2, WCX-2, IMAC-3, LSAX-30, LWCX-30, IMAC-40, PS-10, PS-20 and PG-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, WCX-2, IMAC-3, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 biochip has quaternary ammonium functionalities for anion exchange. The WCX-2 biochip has carboxylate functionalities for cation exchange. The IMAC-3 biochip has nitriloacetic acid functionalities that adsorb transition metal ions, such as $Cu^{++}$ and $Ni^{++}$, by chelation. These immobilized metal ions allow adsorption of peptide and proteins by coordinate bonding. The PS-10 biochip has carboimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached. The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application Ser. No. 09/908,518 (Pohl et al., "Latex Based Adsorbent Chip," Jul. 16, 2002); U.S. patent application 60/350,110 (Um et al., "Hydrophobic Surface Chip," Nov. 8, 2001); U.S. patent application 60/367,837, (Boschetti et al., "Biochips With Surfaces Coated With Polysaccharide-Based Hydrogels," May 5, 2002) and U.S. patent application 60/448,467, entitled "Photocrosslinked Hydrogel Surface Coatings" (Huang et al., filed Feb. 21, 2003).

Various examples of TOF mass spectrometers are shown in FIGS. 1–4, and described below.

FIG. 1 depicts a single-stage ion optic, linear, constant-energy TOF mass spectrometer 100. This figure shows that the spectrometer 100 consists of two portions; an ion acceleration region 102 containing an ion optic assembly 104; and an ion free flight region 106 comprising an ion drift tube. The ion optic assembly 104 consists of a repeller lens element 108 and a ground aperture 110. Two ions, $M_1$ and $M_2$, where $M_2$ is heavier than $M_1$, are accelerated and fly along the free flight region before being detected by the detector 112. The operation of the mass spectrometer depicted in FIG. 1 is described in further detail in "Time-of-flight Mass Spectrometry;" pp. 11915–11984 in the Encyclopedia of Analytical Chemistry; R. A. Meyers (Ed.); John Wiley & Sons Ltd, Chichester, 2000, which is herein incorporated by reference.

Figure 2:
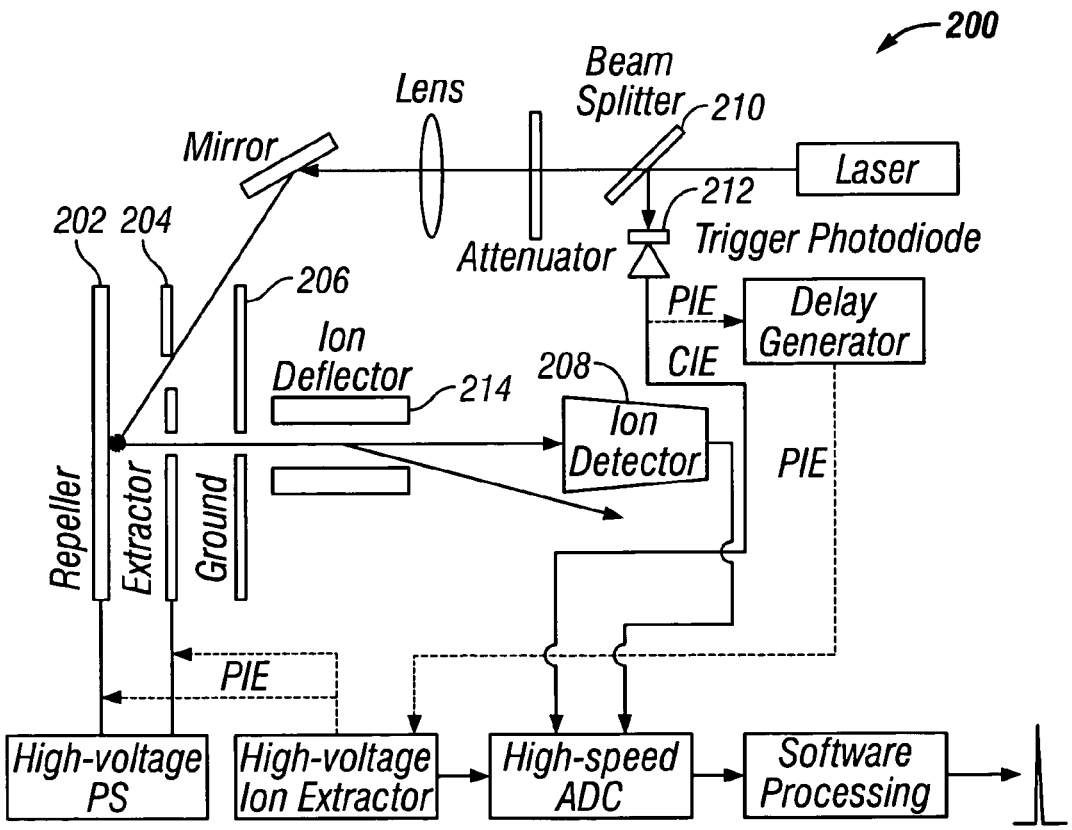
FIG. 2 is a diagram of a parallel extraction, LDI, linear mass spectrometer.

Presently, TOF devices use one of two fundamental schemes of ion extraction: parallel ion extraction and orthogonal ion extraction. FIG. 2 depicts a parallel ion extraction device 200. The energy inherent in a short-duration laser pulse creates ions in a well defined region immediately above a solid probe. As is shown in FIG. 2, the solid probe is contiguous with the repeller lens 202 of the ion optic assembly. In contrast to the simple ion optic assembly of FIG. 1, the assembly of FIG. 2 is a dual-stage design containing an additional plate known as the extractor 204. During ion acceleration, the extractor potential is established to be less than that of the repeller and greater than that of the ground 206. The ion detector 208 incorporates additional systems including ion deflectors 214 such that ions of little interest can be deflected from striking the ion detector. Furthermore, in FIG. 2, an optical beam splitter 210 is used to direct a small portion of the laser beam to strike a trigger photodiode 212 that serves as an event detector. Further details of the operation of the mass spectrometer depicted in FIG. 2 are provided in "Time-of-flight Mass Spectrometry;" pp. 11915–11984 in the Encyclopedia of Analytical Chemistry; R. A. Meyers (Ed.); John Wiley & Sons Ltd, Chichester, 2000, which is herein incorporated by reference.

Figure 3:
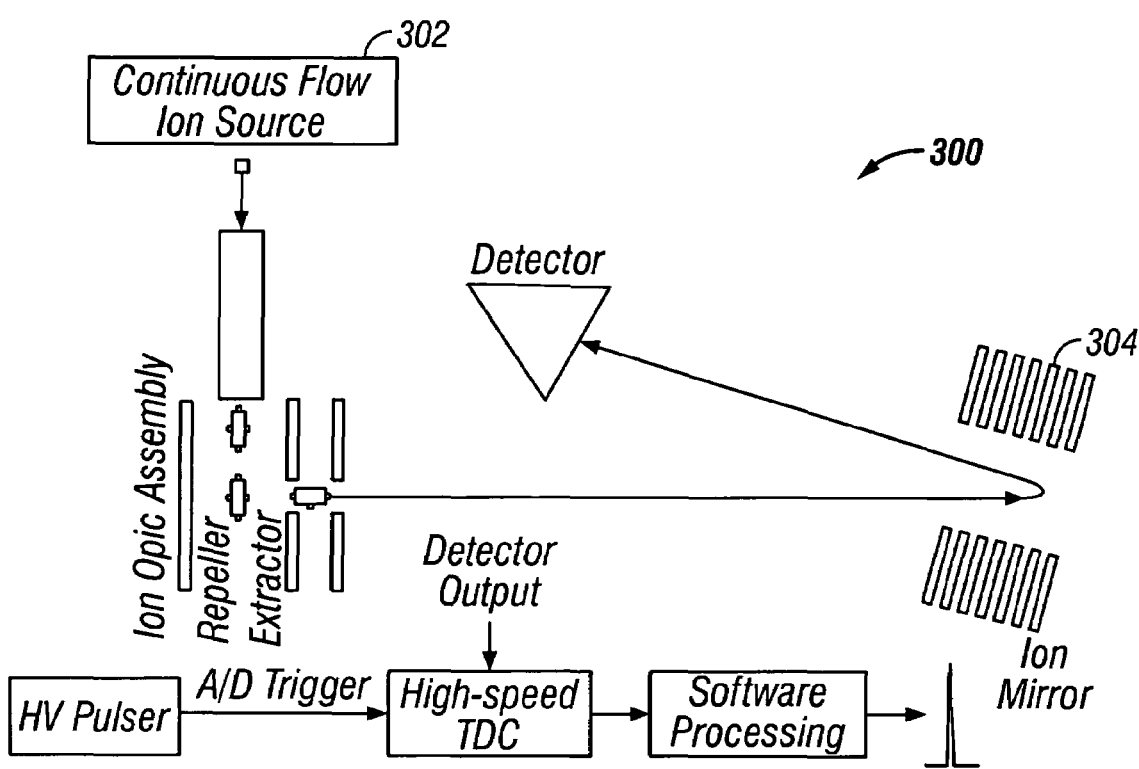
FIG. 3 is a diagram of an orthogonal extraction TOF device with a reflection analyzer.

FIG. 3 illustrates a typical orthogonal extraction TOF device 300 coupled with a continuous flow interface 302. Unlike the linear, parallel extraction geometry of FIG. 2, this analyzer uses an ion mirror 304 or reflection to provide improved mass resolving power. Orthogonal extraction geometries are generally used with dynamic or continuous-flow interfaces. This approach has also been coupled with MALDI. Further details of the operation of the mass spectrometer depicted in FIG. 3 are provided in "Time-of-flight Mass Spectrometry;" pp. 11915–11984 in the Encyclopedia of Analytical Chemistry; R. A. Meyers (Ed.); John Wiley & Sons Ltd, Chichester, 2000, which is herein incorporated by reference.

Figure 4:
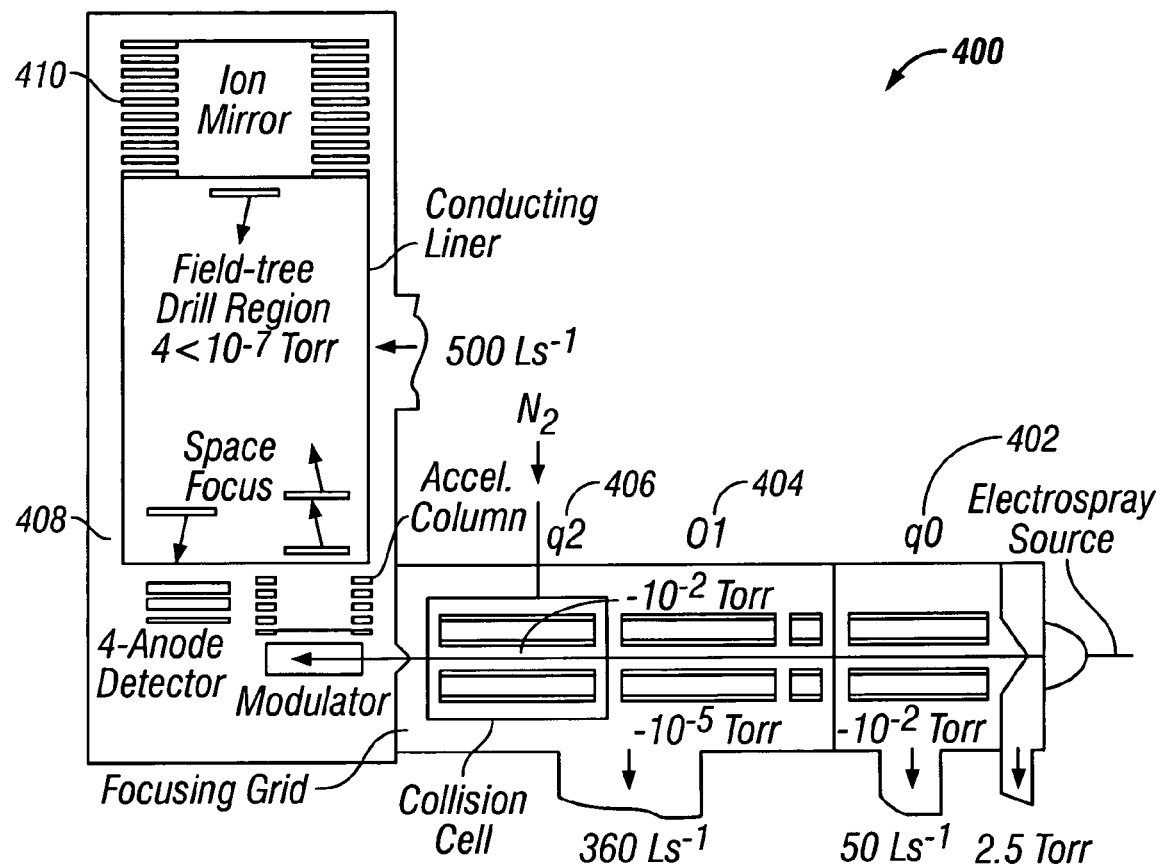
FIG. 4 is a diagram of an orthogonal electrospray TOF device.
Figure 5A:
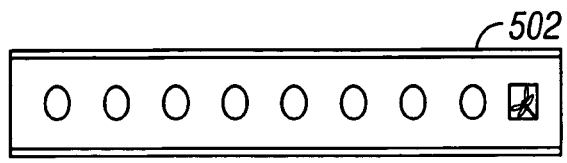
FIG. 5 is a diagram of various modules used for the processing of protein biochip arrays.
Figure 5B:
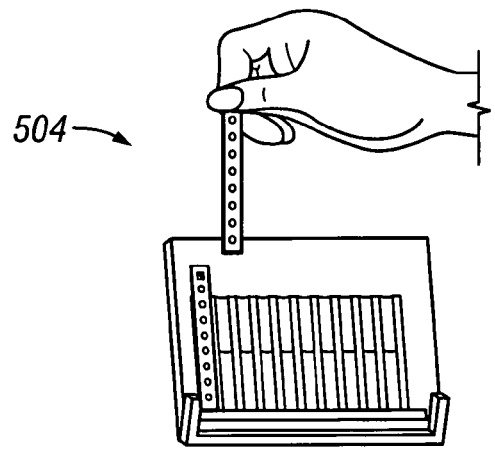
Figure 5C:
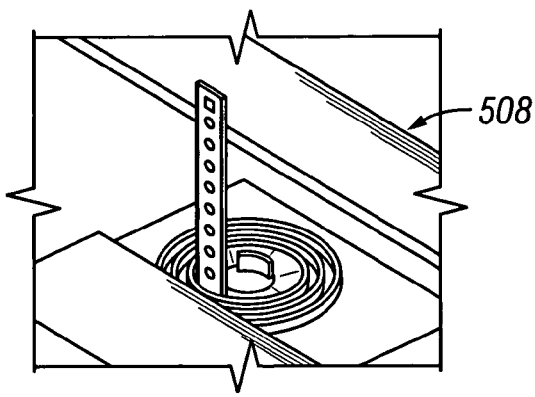
Figure 5D:
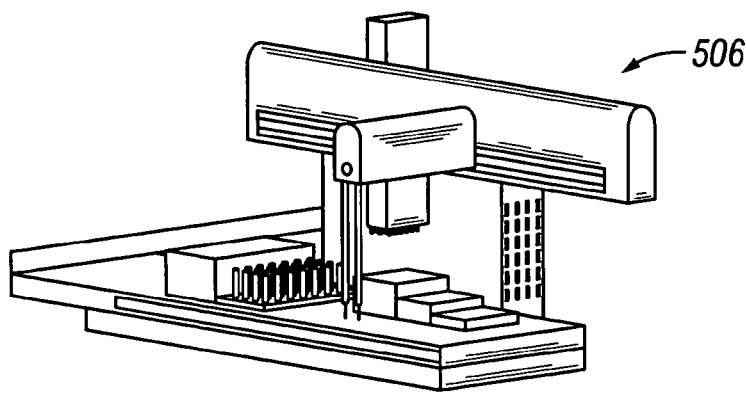

FIG. 4 shows an orthogonal electrospray TOF device 400 equipped with quadrupole ion guide providing collisional cooling 402. Two other quadrupole regions are included for MS purposes, 404 and 406. Time-lag focusing ("TLF") performed in the ion optic assembly 408 corrects for initial spatial distribution, whereas the ion mirror 410 corrects for velocity disparities. TLF and mirrors or reflectors are combined in most modern orthogonal extraction devices to correct for spatial and velocity disparities. Further details of the operation of the mass spectrometer depicted in FIG. 4 are provided in "Time-of-flight Mass Spectrometry;" pp. 11915–11984 in the Encyclopedia of Analytical Chemistry; R. A. Meyers (Ed.); John Wiley & Sons Ltd, Chichester, 2000, which is herein incorporated by reference.

Accordingly, as will be understood by those of skill in the art, the present invention which is related to a fluidic-enabled biochip array and its processing including monitoring and analyzing, may be embodied in other specific forms without departing from the essential characteristics thereof. For example, the array may include discrete regions having a variable density, or that the regions may include lanes that may be used for chromatography. Furthermore, many different surface based analytical techniques may be used to monitor the processing of the array. Accordingly, the foregoing disclosure is intended to be illustrative, but not limiting, of the scope of the invention, which is set forth in the following claims.

What is claimed is:

1. A device, comprising:
   (a) a substrate having a chemically selective surface;
   (b) a fluidic system disposed on said substrate, said fluidic system comprising:
      (i) at least one fluid path in communication with at least a discrete region of said surface, wherein said one fluid path and said discrete region together define a contained sample region on said surface, and
      (ii) a removable fluidic system portion;
   (c) means for fastening the fluidic system to the substrate;
   (d) means for engaging a first detection system, wherein the device is removably insertable into the detection system; and wherein the first detection system comprises means for interrogating the substrate surface when the fluidic system portion is integrated with the device, and
   (e) means for engaging a surface-based analytical tool, wherein the surface-based analytical tool comprises means for interrogating the substrate surface as a result of removal of the fluidic system portion.

2. The device of claim 1 wherein said substrate is adapted for use in a first detection system selected from the group consisting of an optical device, an electrochemical device, an atomic force device, a radio frequency device, a piezoelectric vibrating member, a resonant cantilever device, and combinations thereof.

3. The device of claim 1 wherein said substrate is adapted for use in a surface-based analytical tool selected from the group consisting of a desorption spectrometer and an atomic force device.

4. The device of claim 1 wherein said substrate comprises an optically transparent material.

5. The device of claim 1 wherein said substrate comprises an optically transparent material and said surface comprises a material with a higher refractive index than the substrate.

6. The device of claim 5 wherein said a material with a higher refractive index than the substrate comprises a metal oxide, selected from the group consisting of $Ta_2O_5$, $TiO_2$, $ZrO_2$, $HfO_2$, $SiO_2$, $Si_3N_4$.

7. The device of claim 1 wherein said substrate comprises a grating coupler waveguide that couples through the discrete region.

8. The device of claim 1 wherein said substrate comprises structured electrodes that couple through the discrete region.

9. The device of claim 1 wherein said chemically selective surface comprises a chromatographic capture reagent.

10. The device of claim 1 wherein said chemically selective surface comprises a biospecific capture reagent.

11. The device of claim 1 wherein said chemically selective surface comprises a reactive moiety capable of binding a capture reagent.

12. The device of claim 1 wherein said chemically selective surface comprises a material that supports desorption and ionization of adsorbed species upon laser irradiation.

13. The device of claim 1 wherein said sample region includes a chromatographic stationary phase, said stationary phase configured to perform thin layer, open tubular, capillary, packed, gel or retentate chromatography.

14. The device of claim 13 wherein said stationary phase is the chemically selective surface of the region.

15. The device of claim 13 comprising a plurality of stationary phases arranged serially within the device, so as to perform multi-stage chromatography.

16. The device of claim 1 wherein the fluid path comprises an inlet port configured to accept fluid from a fluid delivery system.

17. The device of claim 1 wherein the fluidic system comprises a first solid portion and a gasket, wherein the gasket is in contact with the substrate.

18. The device of claim 1 wherein said at least one fluid path is in communication with a plurality of discrete portions of said surface.

19. The device of claim 1 wherein said fluid path comprises at least one diaphragm valve.

20. The device of claim 1 wherein said system comprises a plurality of fluid paths in fluid communication with said same sample region.

21. The device of claim 1 wherein said fluidic system comprises the means for fastening to the substrate.

22. The device of claim 1 wherein the fluidics system comprises an electrophoretic separation column.

23. The device of claim 1 wherein the entire fluidic system is removable from the device.

24. The device of claim 1 wherein said means for fastening comprises a holder that receives the fluidics system and receives the substrate between the fluidics system and the holder.

25. The device of claim 1 wherein said means for fastening comprises a holder that receives the fluidics system and receives the substrate between the fluidics system and the holder and further comprises a pin that holds the fluidics system to the holder.

26. The device of claim 1 wherein said means for fastening comprises a first frame that receives the fluidics system and a second frame comprising a surface complementarily shaped with respect to the first frame to securely hold the fluidics system inside the first frame.

27. The device of claim 1 wherein said removable fluidics portion is peelably removable from the device.

28. The device of claim 1 wherein said removable fluidics portion is removably fastened to device by mechanical means, adhesive means or frangible attachment to the fluidics system.

29. A method for detecting an analyte, comprising:
providing a substrate having a chemically selective surface, and wherein said substrate is attached with a fluidic system;
delivering a sample comprising an analyte using said fluidic system to at least one sample region on said substrate;
monitoring physicochemical changes of said surface in response to said analyte;
removing a portion of said fluidic system to render a portion of said surface directly interrogatable by a surface based analytical technique; and
detecting physicochemical changes of the surface region.

30. The method of claim 29 further comprising interrogating said surface after said removing using LDI-MS.

31. The method of claim 29 wherein said providing comprises
providing a chemically selective surface comprising a reactive moiety and delivering to said sample region a capture reagent that is bound by said reactive moiety.

32. The method of claim 29 wherein said providing comprises
providing a selective surface comprising a moiety and delivering to said sample region a capture reagent that is bound by said moiety by physi-sorption.

33. The method of claim 29 further comprising delivering a conditioning fluid to said surface after said delivering said sample.

34. The method of claim 29 further comprising delivering a reagent to selectively functionalize said surface after said delivering said sample.

35. The method of claim 29 further comprising delivering said sample to a plurality of discrete locations on said surface.

36. The method of claim 29 wherein said sample is one of a plurality of samples and said sample region is one of a plurality of different sample regions and said delivering comprises delivering each of said plurality of samples to said different sample regions.

37. The method of claim 29 further comprising delivering a matrix solution to said sample region before said removing.

38. The method of claim 29 wherein said monitoring is selected from the group consisting of optical monitoring, electrochemical monitoring, atomic force monitoring, a radio frequency monitoring, a piezoelectric vibrating member monitoring, a resonate cantilever device monitoring, and combinations thereof.

39. The method of claim 38 wherein said optical-based monitoring is configured to monitor changes in properties of polarization of light caused by interaction of light with said surface.

40. The method of claim 38 wherein said properties are selected from a group consisting of fluorescence, luminescence, chemiluminescence, absorbance, reflectance, transmittance, birefringence, refractive index and combinations thereof.

41. The method of claim 38 wherein said optical monitoring comprises using an optical-based device that is configured to detect changes in the refractive index at the surface.

42. The method of claim 38 wherein said optical monitoring comprises using an optical-based device that comprises a grating coupler waveguide device.

43. The method of claim 42 wherein said grating coupler waveguide device is interrogated by varying the wavelength of incident radiation at a fixed angle and determining the wavelength of maximum coupling.

44. The method of claim 42 wherein said grating coupler waveguide device is interrogated by varying the angle of the incident light of a fixed wavelength and determining the angle of maximum coupling.

45. The method of claim 42 wherein said grating coupler waveguide device is interrogated by illuminating said grating coupler device with light comprising a range of wavelengths and determining the wavelength of maximum coupling by measuring the wavelength of the coupled light.

46. The method of claim 42 wherein said grating coupler waveguide device is interrogated by illuminating said grating coupler device with light of a fixed wavelength over a range of angles and determining the angle of the coupled light.

47. The method of claim 42 wherein said grating coupler waveguide device is interrogated by a combination of
varying the wavelength of incident radiation at a fixed angle and determining the wavelength of maximum coupling,
varying the angle of the incident light of a fixed wavelength and determining the angle of maximum coupling,
illuminating said grating coupler device with light comprising a range of wavelengths and determining the wavelength of maximum coupling by measuring the wavelength of the coupled light, and
illuminating said grating coupler device with light of a fixed wavelength over a range of angles and determining the angle of the coupled light.

48. The method of claim 29 further comprising providing a substrate wherein the substrate comprises means for rendering the substrate compatible with a device for monitoring physiochemical changes of said surface.

49. The method of claim 48 wherein said monitoring comprises an optical monitoring and the means comprise an optically transmissive path communicating with said surface said path selected from a window, a lens, a prism, a surface planar waveguide or a fiber optic.

50. The method of claim 48 wherein said monitoring comprises an optical monitoring and the means is selected from a polarizer, a lens, a mirror, a diffraction grating, a wave plate, an attenuator, an interferometer and combinations thereof.

51. The method of claim 48 wherein said monitoring comprises an electrochemical monitoring and the means comprise electrodes in electrical communication with said surface.

52. The method of claim 48 wherein said monitoring comprises using an atomic force microscope (AFM) and the means comprise an AFM probe or port for accepting an AFM probe in physical communication with said surface.

53. The method of claim 48 wherein said monitoring comprises using a radio frequency device and the means comprise a radiofrequency waveguide in radio frequency communication with said surface.

54. The method of claim 29 wherein said sample region comprises:
a thin-layer chromatographic surface and said delivering comprises
flowing said sample across said chromatographic surface, and
chromatographically separating said analyte in said sample region.

55. The method of claim 54 wherein the chromatographically separating is selected from a group consisting of Reverse Phase, ion exchange, mixed mode, normal phase, immobilized metal affinity capture, affinity capture, and combinations thereof.

56. The method of claim 54 wherein said chromatographically separating comprises:
monitoring said chromatographic surface at a plurality of locations; and
detecting analytes bound to said capture reagent at said plurality of locations.

57. The method of claim 29 further comprising prior electrophoresis of the sample, said electrophoresis including capillary denaturing, nascent, free zone, isoelectric focusing, isotachophoresis, gel electrophoresis, or combinations thereof.

58. A detection system comprising:
(a) a device comprising;
(1) a substrate having a chemically selective surface;
(2) a fluidic system disposed on said substrate, said fluidic system comprising:
(i) at least one fluid path in communication with at least a discrete region of said surface, wherein said one fluid path and said discrete region together define a contained sample region on said surface, and
(ii) a removable fluidic system portion;
(3) means for fastening the fluidic system to the substrate;
(4) means for engaging a first detection system, wherein the device is removably insertable into the detection system; and wherein the first detection system comprises means for interrogating the substrate surface when the fluidic system portion is integrated with the device, and
(5) means for engaging a surface-based analytical tool, wherein the surface-based analytical tool comprises means for interrogating the substrate surface as a result of removal of the fluidic system portion;
(b) means for interrogating the substrate surface when the fluidic system port ion is coupled with the device.

59. The detection system of claim 58 wherein said means for interrogating comprises an optical device and the means for engaging comprise an optically transmissive path communication with said surface, said path selected from a window, a lens, a prism, a surface planar waveguide or a fiber optic.

60. The detection system of claim 59 wherein said optical device is configured to monitor changes in properties of the polarization of light caused by interaction of light with said surface.

61. The detection system of claim 59 wherein said optical device is configured to monitor properties of said surface selected from a group consisting of fluorescence, luminescence, chemiluminescence, absorbance, reflectance, transmittance, birefringence, refractive index and combinations thereof.

62. The detection system of claim 59 wherein said optical device is configured to detect changes in the refractive index at said surface.

63. The detection system of claim 62 wherein said waveguide is interrogated by varying the wavelength of incident radiation at a fixed angle and determining the wavelength of maximum coupling.

64. The detection system of claim 62 wherein said waveguide is interrogated by varying the angle of the incident light of a fixed wavelength and determining the angle of maximum coupling.

65. The detection system of claim 62 wherein said waveguide is interrogated by illuminating said grating coupler device with light comprising a range of wavelengths and determining the wavelength of maximum coupling by measuring the wavelength of the coupled light.

66. The detection system of claim 62 wherein said waveguide is interrogated by illuminating said grating coupler device with light of a fixed wavelength over a range of angles and determining the angle of the coupled light.

67. The detection system of claim 62 wherein said waveguide is interrogated by a combination of
varying the wavelength of incident radiation at a fixed angle and determining the wavelength of maximum coupling,
varying the angle of the incident light of a fixed wavelength and determining the angle of maximum coupling,
illuminating said grating coupler device with light comprising a range of wavelengths and determining the wavelength of maximum coupling by measuring the wavelength of the coupled light, and
illuminating said grating coupler device with light of a fixed wavelength over a range of angles and determining the angle of the coupled light.

68. The detection system of claim 59 wherein said substrate comprises a grating coupler waveguide.

69. The detection system of claim 58 wherein said means for interrogating comprises an optical device and the means for engaging a first detection system is selected from a polarizer, a lens, a mirror, a diffraction grating, a diffractive element, a wave plate, an attenuator, an interferometer and combinations thereof.

70. The detection system of claim 58 wherein said means for interrogating comprises an electrochemical device and the means for engaging a first detection system comprise electrodes in electrical communication with said surface.

71. The device of claim 58 wherein said means for interrogating comprises a radio frequency device and the means for engaging a first detection system comprise a radiofrequency waveguide in radio frequency communication with said surface.

72. A devices comprising:
(a) a substrate;
(b) a fluidic system disposed on said substrate, said fluidic system comprising:

(i) at least one fluid path in communication with at least a discrete region of the surface of said substrate, wherein said one fluid path and said discrete region together define a contained sample region on said surface, and
(ii) a removable fluidic system portion;
(iii) a remaining portion of the fluidic system that remains after removal of the removable portion, said remaining portion comprising at least one electrostatic and, or pneumatic element;
(c) means for engaging a surface-based analytical tool, wherein the surface-based analytical tool comprises means for interrogating the substrate surface as a result of removal of the fluidic system portion.

* * * * *